(12) United States Patent
Shilev et al.

(10) Patent No.: US 11,844,493 B2
(45) Date of Patent: Dec. 19, 2023

(54) ELECTROSURGICAL APPARATUS WITH DYNAMIC LEAKAGE CURRENT COMPENSATION AND DYNAMIC RF MODULATION

(71) Applicant: Apyx Medical Corporation, Clearwater, FL (US)

(72) Inventors: Nikolay Dimitrov Shilev, Sofia (BG); Viktor Tomov Tomov, Sofia (BG)

(73) Assignee: Apyx Medical Corporation, Clearwater, FL (US)

( * ) Notice: Subject to any disclaimer, the term of this patent is extended or adjusted under 35 U.S.C. 154(b) by 656 days.

(21) Appl. No.: 16/461,609

(22) PCT Filed: Nov. 17, 2017

(86) PCT No.: PCT/US2017/062195
§ 371 (c)(1),
(2) Date: May 16, 2019

(87) PCT Pub. No.: WO2018/094159
PCT Pub. Date: May 24, 2018

(65) Prior Publication Data
US 2020/0060749 A1    Feb. 27, 2020

Related U.S. Application Data

(60) Provisional application No. 62/423,379, filed on Nov. 17, 2016.

(51) Int. Cl.
*A61B 18/12* (2006.01)
*A61B 18/04* (2006.01)
(Continued)

(52) U.S. Cl.
CPC ........ *A61B 18/1206* (2013.01); *A61B 18/042* (2013.01); *A61B 2017/00376* (2013.01);
(Continued)

(58) Field of Classification Search
CPC .............. A61B 18/1206; A61B 18/042; A61B 2018/00601; A61B 2018/00607;
(Continued)

(56) References Cited

U.S. PATENT DOCUMENTS 3,683,923 A    8/1972  Anderson
3,946,738 A    3/1976  Newton et al.
(Continued)

FOREIGN PATENT DOCUMENTS

| EP | 2851029 | 3/2015 |
|---|---|---|
| JP | 2000041993 A | 2/2000 |
| WO | WO9424949 | 11/1994 |

OTHER PUBLICATIONS

European Search Report for European Application No. 17870880.6; dated Jun. 3, 2020; nine (9) pages.
(Continued)

*Primary Examiner* — Joseph A Stoklosa
*Assistant Examiner* — Annie L Shoulders
(74) *Attorney, Agent, or Firm* — Gerald E. Hespos; Michael J. Porco

(57) ABSTRACT

The present disclosure is directed toward an electrosurgical apparatus including an electrosurgical generator that may be coupled to an electrosurgical applicator. In one aspect of the present disclosure, a controller of the electrosurgical generator is configured to execute a dynamic leakage current compensation algorithm or function to compensate for the leakage current of an electrosurgical applicator and accompanying cable coupling the electrosurgical applicator to electrosurgical generator. In another aspect of the present disclosure, the controller of the electrosurgical generator is configured to execute a dynamic radio frequency modulation algorithm or function to dynamically control the crest factor of the output waveform of the electrosurgical generator (Continued)

SIMPLIFIED FLOW CHART OF THE DYNAMIC LEAKAGE CURRENT COMPENSATION ALGORITHM.

based on the measured impedance across an active and return terminal of the electrosurgical generator.

20 Claims, 16 Drawing Sheets

(51) Int. Cl.
  *A61B 17/00* (2006.01)
  *A61B 18/00* (2006.01)
  *A61B 18/14* (2006.01)
  *A61B 17/3203* (2006.01)
(52) U.S. Cl.
  CPC ............... *A61B 2017/32035* (2013.01); *A61B 2018/0091* (2013.01); *A61B 2018/00601* (2013.01); *A61B 2018/00607* (2013.01); *A61B 2018/00648* (2013.01); *A61B 2018/00684* (2013.01); *A61B 2018/00845* (2013.01); *A61B 2018/00875* (2013.01); *A61B 2018/00892* (2013.01); *A61B 2018/126* (2013.01); *A61B 2018/144* (2013.01); *A61B 2018/1412* (2013.01); *A61B 2018/1417* (2013.01); *A61B 2018/1425* (2013.01)
(58) Field of Classification Search
  CPC .. A61B 2018/00875; A61B 2018/1417; A61B 2018/1412; A61B 2017/00376; A61B 2017/32035
  See application file for complete search history.

(56) References Cited

U.S. PATENT DOCUMENTS

| | | | |
|---|---|---|---|
| 4,094,320 A | | 6/1978 | Newton et al. |
| 4,200,105 A | | 4/1980 | Gonser |
| 4,437,464 A | | 3/1984 | Crow |
| 4,662,369 A | | 5/1987 | Ensslin |
| 4,903,696 A | * | 2/1990 | Stasz ................. A61B 18/1206 606/37 |
| 5,152,762 A | * | 10/1992 | McElhenney ...... A61B 18/1233 606/35 |
| 5,312,401 A | | 5/1994 | Newton et al. |
| 5,372,596 A | | 12/1994 | Klicek et al. |
| 5,432,459 A | | 7/1995 | Thompson et al. |
| 5,436,566 A | | 7/1995 | Thompson et al. |
| 5,688,269 A | | 11/1997 | Newton et al. |
| 5,769,841 A | | 6/1998 | Odell et al. |
| 5,895,386 A | | 4/1999 | Odell et al. |
| 5,936,536 A | | 8/1999 | Morris |
| 6,203,516 B1 | * | 3/2001 | Kepley ............... A61F 9/00745 604/22 |
| 6,245,063 B1 | | 6/2001 | Uphoff |
| 6,494,877 B2 | | 12/2002 | Odell et al. |
| 8,100,897 B2 | | 1/2012 | Zoran |
| 8,226,640 B2 | | 7/2012 | Zoran |
| 8,430,873 B2 | | 4/2013 | Gregg |
| 8,979,834 B2 | | 3/2015 | Zoran et al. |
| 2001/0031992 A1 | | 10/2001 | Fishler et al. |
| 2002/0161306 A1 | | 10/2002 | Govari |
| 2003/0233088 A1 | | 12/2003 | Ohyama et al. |
| 2004/0015163 A1 | | 1/2004 | Buysse et al. |
| 2007/0173811 A1 | | 7/2007 | Couture et al. |
| 2008/0082095 A1 | * | 4/2008 | Shores ............... A61B 18/1206 606/34 |
| 2011/0025348 A1 | | 2/2011 | Chetham et al. |
| 2011/0221463 A1 | | 9/2011 | Livneh |
| 2012/0109121 A1 | | 5/2012 | Gregg |
| 2012/0123408 A1 | | 5/2012 | Zoran |
| 2013/0197510 A1 | * | 8/2013 | Heckel ............... A61B 18/1402 606/41 |
| 2013/0267943 A1 | | 10/2013 | Hancock |
| 2014/0276754 A1 | * | 9/2014 | Gilbert ............... A61B 18/1815 606/33 |
| 2015/0025523 A1 | * | 1/2015 | Friedrichs .......... A61B 18/1206 606/34 |
| 2015/0196344 A1 | | 7/2015 | Wham et al. |
| 2015/0320477 A1 | * | 11/2015 | Hagg ................. A61B 18/1206 606/37 |
| 2016/0001081 A1 | | 1/2016 | Parker et al. |
| 2016/0045247 A1 | | 2/2016 | Heim |
| 2016/0143685 A1 | * | 5/2016 | Friedrichs .......... A61B 18/1206 606/34 |
| 2016/0310202 A1 | * | 10/2016 | Wham ............... A61B 18/1233 |
| 2016/0324537 A1 | * | 11/2016 | Green ............ A61B 17/320092 |
| 2017/0189101 A1 | * | 7/2017 | Yates ................. A61B 18/1445 |

OTHER PUBLICATIONS

International Search Report and Written Opinion for PCT Application No. PCT/US2017/062195; dated Jan. 26, 2018; nine (9) pages.
Ming-Ping Wu et al., "Complications and Recommended Practices for Electrosurgery in Laparoscopy", Am J Surg.Jan. 2000; 179:67-73.
The Electroscope Electroshield System; Electroscope, Inc. Boulder, CO; Sep. 7, 2000.

* cited by examiner

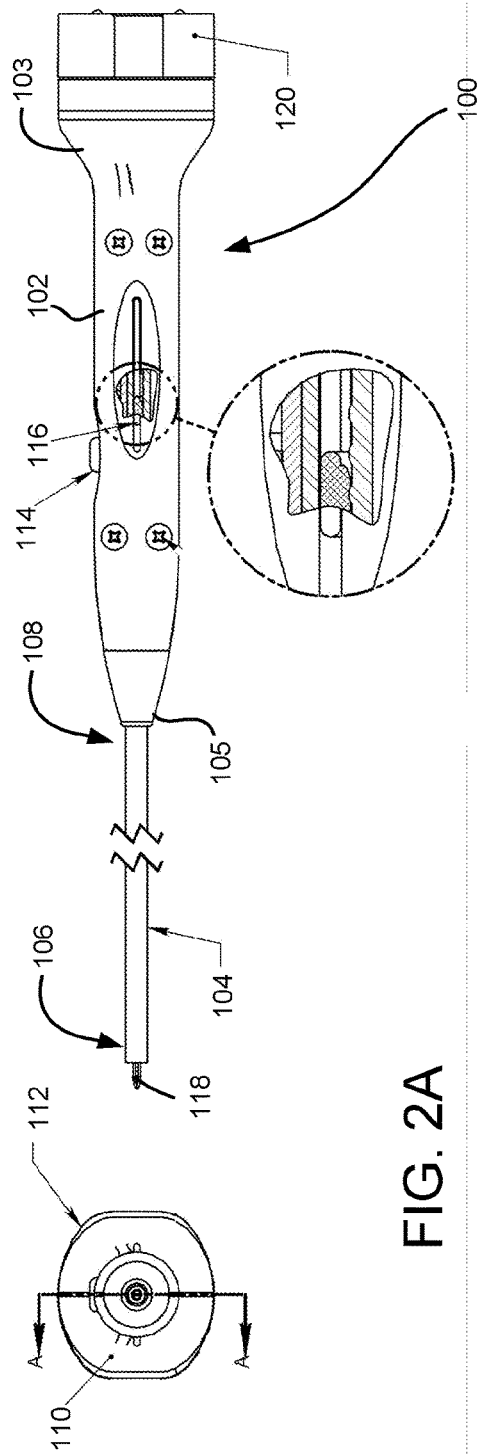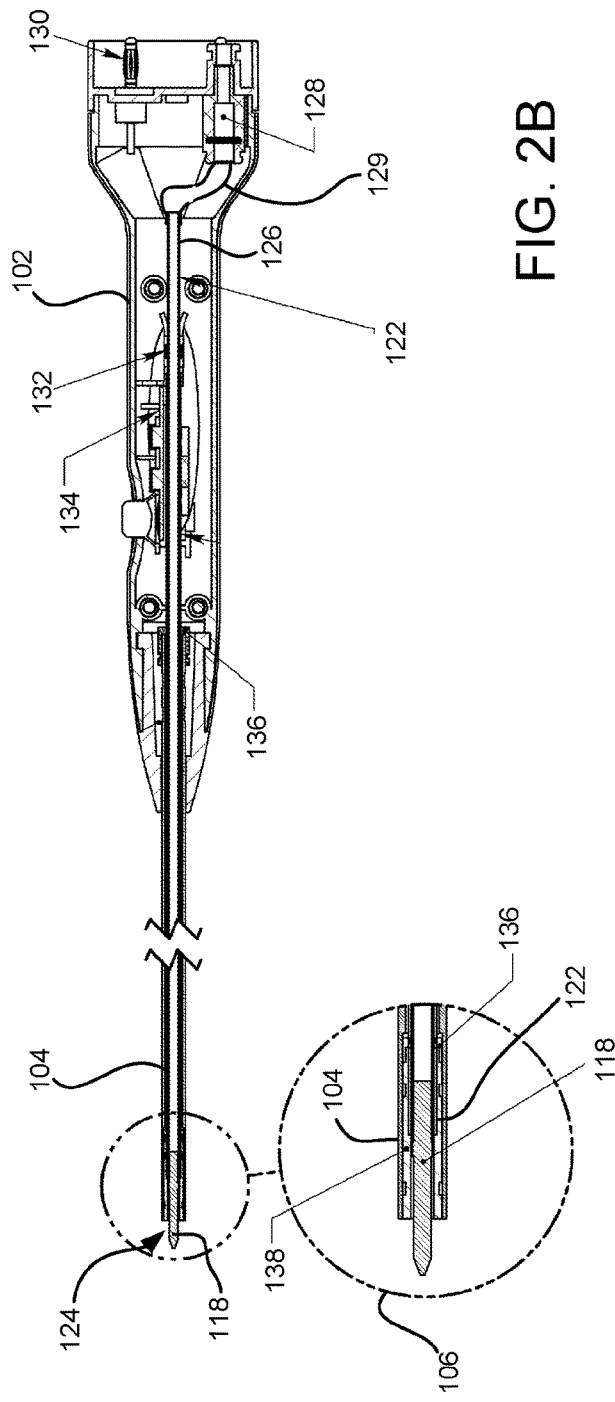
FIG. 2A
FIG. 2B

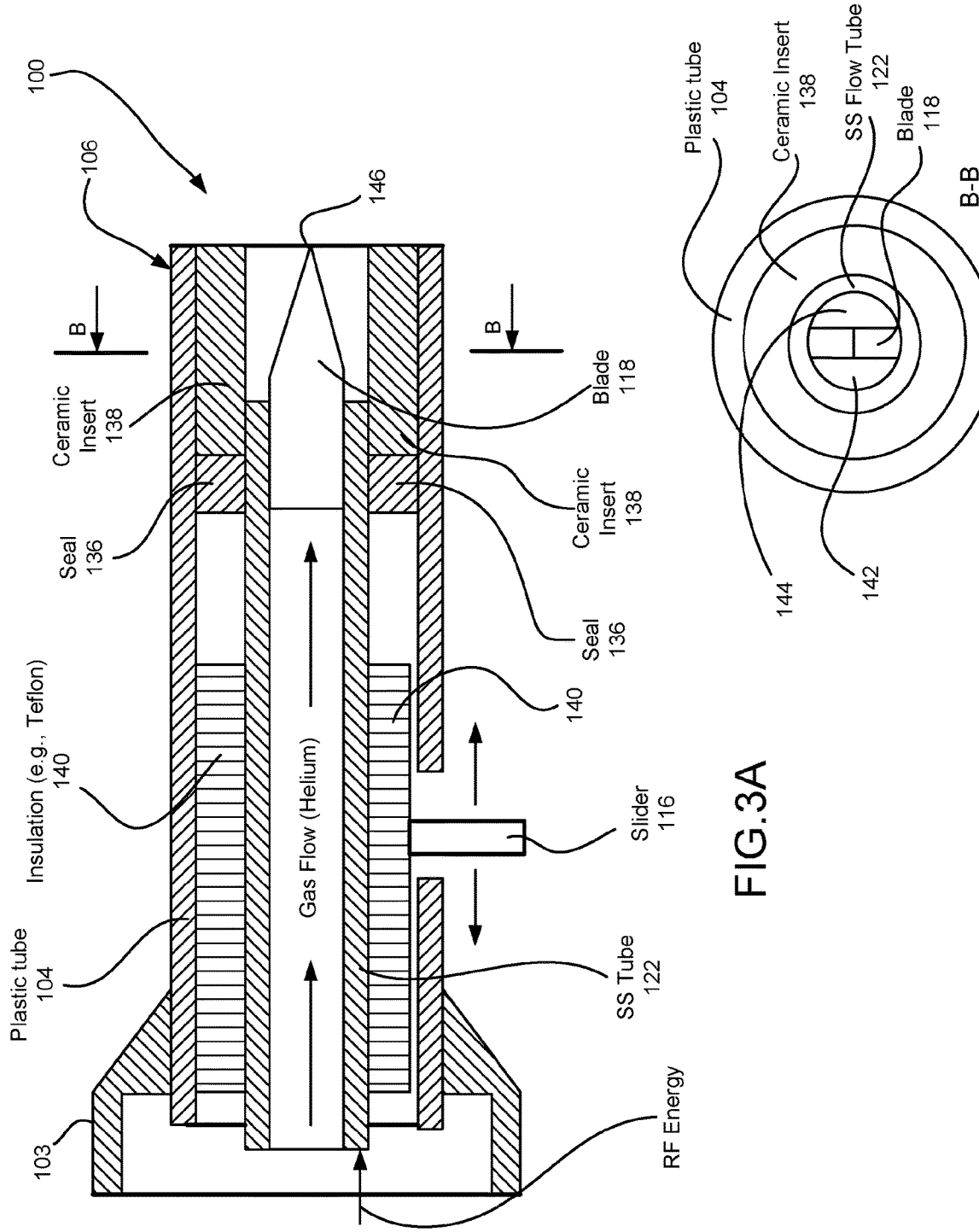

DISTRIBUTED ELEMENT MODEL OF THE ESU ACCESSORY.

LUMPED ELEMENT MODEL OF THE ESU ACCESSORY.

SIMPLIFIED EQUIVALENT LOAD CIRCUIT ON THE OUTPUT TERMINALS OF THE ESU.

EQUIVALENT LOAD CIRCUIT FOR WHEN PERFORMING LEAKAGE COMPENSATION.

EQUIVALENT MODEL OF THE ESU OUTPUT LOAD CIRCUIT.

SIMPLIFIED FLOW CHART OF THE DYNAMIC LEAKAGE CURRENT COMPENSATION ALGORITHM.

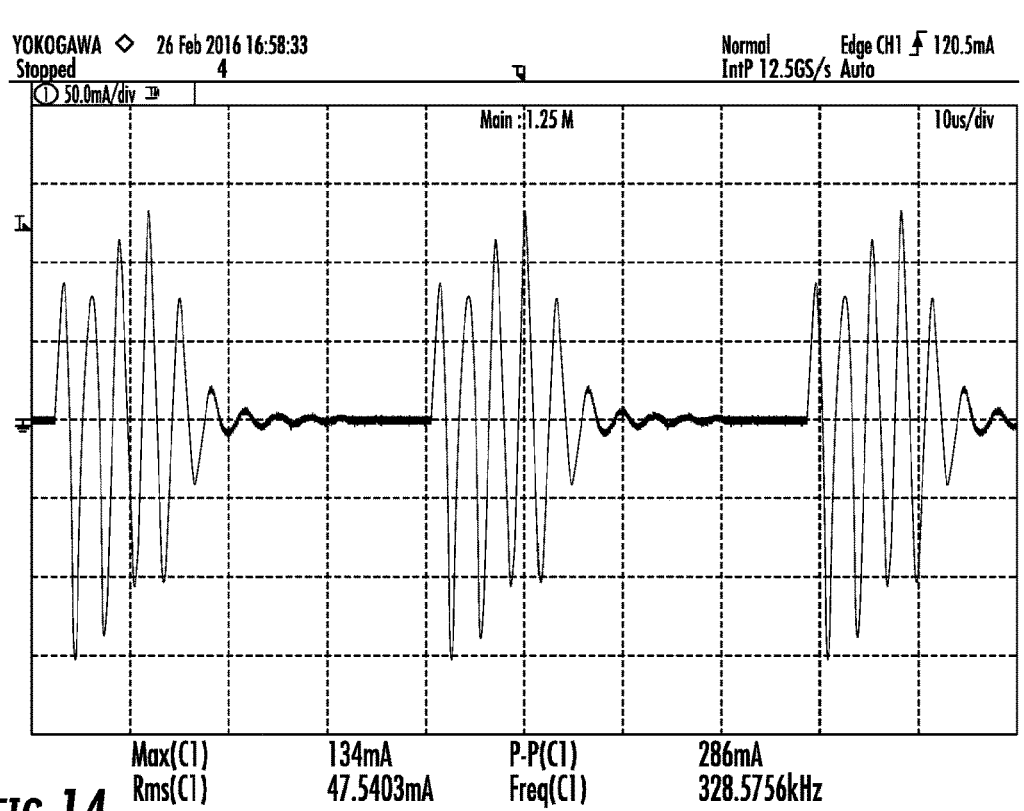
FIG. 14 OUTPUT CURRENT WAVEFORM MEASURED AT 40W AND 20 kΩ.
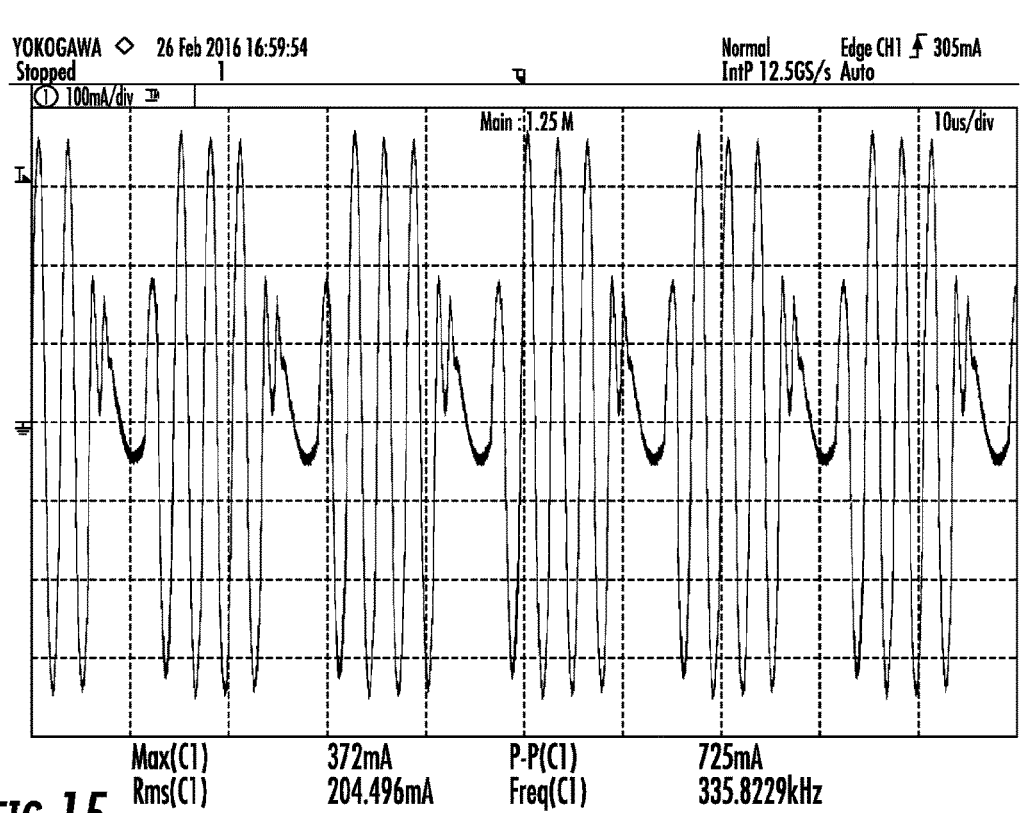
FIG. 15 OUTPUT CURRENT WAVEFORM MEASURED AT 40W AND 1000 Ω.

ELECTROSURGICAL APPARATUS WITH DYNAMIC LEAKAGE CURRENT COMPENSATION AND DYNAMIC RF MODULATION

PRIORITY

This application claims priority to U.S. Provisional Patent Appl. No. 62/423,379 filed Nov. 17, 2016, entitled "ELECTROSURGICAL APPARATUS", the contents of which are hereby incorporated by reference in its entirety.

BACKGROUND

Field

The present disclosure relates generally to electrosurgery and electrosurgical systems and apparatuses, and more particularly, to an electrosurgical apparatus with an integrated closed loop system.

Description of the Related Art

High frequency electrical energy has been widely used in surgery. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. In the latter example, the process can be relatively slow, generate large volumes of noxious smoke with vaporized and charred tissue, and may cause collateral damage to surrounding healthy tissue when high power electrosurgical energy is used. Precision accuracy can also be a problem, due to the width of the plasma beam. Often, a simple surgical knife is used to excise the tissue in question, followed by the use of a cold plasma applicator for cauterization, sterilization, and hemostasis.

Medical devices used in the afore-mentioned electrosurgery and plasma-beam surgery typically consist of a generator unit and an attached hand piece or applicator. A variety of different applicators may be available for a given generator unit, some of which are general purpose, and others designed for a specific task.

SUMMARY

The present disclosure is directed toward an electrosurgical system including an electrosurgical generator that may be coupled to an electrosurgical applicator. In one aspect of the present disclosure, a controller of the electrosurgical generator is configured to execute a dynamic leakage current compensation algorithm or function to compensate for a leakage current of an electrosurgical applicator and associated cable accessory coupled the electrosurgical generator. In another aspect of the present disclosure, the controller of the electrosurgical generator is configured to execute a dynamic radio frequency (RF) modulation algorithm or function to dynamically control the crest factor of an output waveform of the electrosurgical generator based on a measured impedance across an active and return terminal of the electrosurgical generator.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is a schematic diagram of an electrosurgical apparatus in accordance with an embodiment of the present disclosure;

FIG. 2B is a cross sectional view of the electrosurgical apparatus shown in FIG. 2A taken along line A-A;

FIG. 3A is an enlarged cross sectional view of the electrosurgical apparatus in accordance with an embodiment of the present disclosure;

FIG. 3B illustrates a front view of the electrosurgical apparatus shown in FIG. 3A taken along line B-B;

FIG. 14 is a graph including measurements of a 20 kΩ output load in accordance with an embodiment of the present disclosure;

FIG. 15 is a graph including measurements of a 1000Ω output load in accordance with an embodiment of the present disclosure;

Figure 1:
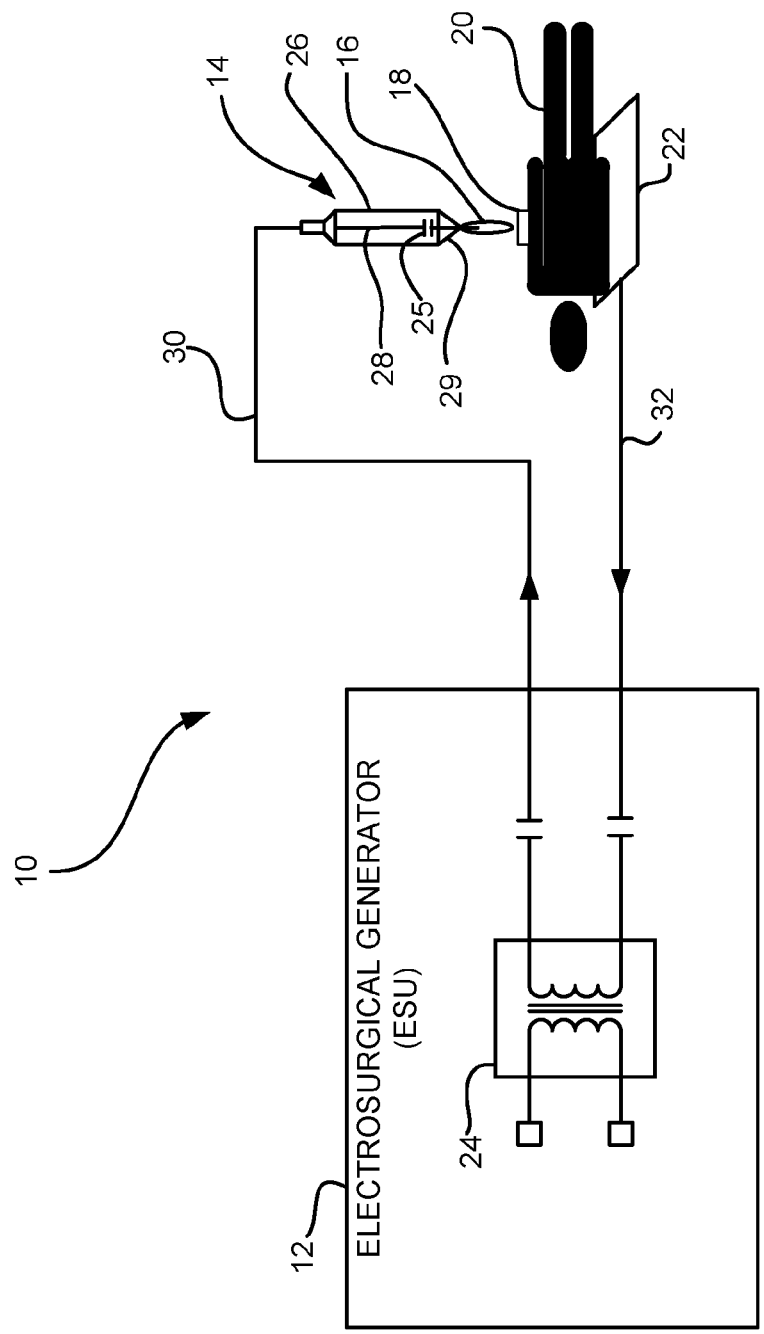
FIG. 1 is an illustration of an exemplary monopolar electrosurgical system in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

FIG. 1 shows an exemplary monopolar electrosurgical system generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20. Furthermore, a current limiting capacitor 25 is provided in series with the electrode 28 to limit the amount of current being delivered to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference.

It is to be appreciated that transformer 24 may be disposed in the plasma generator handpiece 26, as will be described in various embodiments below. In this configuration, other transformers may be provided in the generator 12 for providing a proper voltage and current to the transformer in the handpiece, e.g., a step-down transformer, a step-up transformer or any combination thereof.

Referring to FIG. 2A, an electrosurgical apparatus 100 in accordance with the present disclosure is illustrated. Generally, the apparatus 100 includes a housing 102 having a proximal end 103 and a distal end 105 and a tube 104 having an open distal end 106 and a proximal end 108 coupled to the distal end 105 of the housing 102. The housing 102 includes a right side housing 110 and left side housing 112, and further includes provisions for a button 114 and slider 116. Activation of the slider 116 will expose a blade 118 at the open distal end 106 of the tube 104. Activation of the button 114 will apply electrosurgical energy to the blade 118 and, in certain embodiments, enable gas flow through the flow tube 122, as will be described in detail below.

Additionally, a transformer 120 is provided on the proximal end 103 of the housing for coupling a source of radio frequency (RF) energy to the apparatus 100. By providing the transformer 120 in the apparatus 100 (as opposed to locating the transformer in the electrosurgical generator), power for the apparatus 100 develops from higher voltage and lower current than that required when the transformer is located remotely in the generator, which results in lower thermalization effects. In contrast, a transformer back in the generator produces applicator power at a lower voltage, higher current with greater thermalization effects. Therefore, by providing the transformer 120 in apparatus 100, collateral damage to tissue at the operative site is minimized.

A cross section view along line A-A of the apparatus 102 is shown in FIG. 2B. Disposed within the housing 102 and tube 104 is flow tube 122 which runs along the longitudinal axis of the apparatus 100. On a distal end 124 of the flow tube 122, the blade 118 is retained within the flow tube 122. A proximal end 126 of the flow tube 122 is coupled to a source of gas via a tube connector 128 and flexible tubing 129. The proximal end 126 of the flow tube 122 is also coupled to a source of RF energy via plug 130 which couples to transformer 120. The flow tube 122 is made of an electrically conducting material, preferably stainless steel, as to conduct the RF energy to the blade 118 when being employed for plasma applications or electrosurgical cutting as will be described below. The outer tube 104 is constructed from non-conductive material, e.g., Lestran. The slider 116 is coupled to the flow tube 122 via a retaining collar 132. A printed circuit board (PCB) 134 is disposed in the housing 102 and controls the application of the RF energy from the transformer 120 via the button 114.

It is to be appreciated that the slider 116 may be freely moveable in a linear direction or may include a mechanism for incremental movements, e.g., a ratchet movement, to prevent an operator of the apparatus 100 from over extending the blade 118. By employing a mechanism for incremental movements of the blade 118, the operator will have greater control over the length of the exposed blade 118 to avoid damage to tissue at the surgical site.

An enlarged view of the distal end 106 of the outer tube 104 is also illustrated in FIG. 2B. Here, the blade 118 is coupled to the flow tube 122 which is held in place in the outer tube 104 by at least one seal 136. The at least one seal 136 prevents backflow of gas into tube 104 and housing 102. A cylindrical ceramic insert 138 is disposed in the distal end of the outer tube 104 to maintain the blade along the longitudinal axis of the apparatus 100 and provide structural support during mechanical cutting when the blade is exposed beyond the distal end of the outer tube 104.

The operational aspect of the apparatus 100 will now be described in relation to FIGS. 3A and 3B, where FIG. 3A shows an enlarged cross section of the apparatus and FIG. 3B illustrates a front view of the apparatus.

Referring to FIG. 3A, the flow tube 122 is disposed in the outer tube 104 with a cylindrical insulator 140 disposed around the flow tube 122. Slider 116 is coupled to the insulator 140 and is employed to extend and retract the blade 118. At the distal end 106 of the outer tube 104, the annular or ring shaped seal 136 and cylindrical ceramic insert 138 are disposed about the flow tube 122. As can be seen in FIG. 3B, the generally planar blade 118 is coupled to an inner circumference of the cylindrical flow tube 122 such that two gas passageways 142, 144 are formed on the both sides of the blade 118. As gas flows from the proximal end 103 of the housing through the flow tube 122, the gas will pass over the blade 118 out the distal end 106 of the outer tube 104.

When the blade is in the retracted position as shown in FIG. 3A, the apparatus 100 is suitable for generating plasma. In the retracted position, RF energy is conducted to a tip 146 of the blade 118 from an electrosurgical generator (not shown) via the flow tube 122. An inert gas, such as helium or argon, is then supplied to the flow tube from either the electrosurgical generator or an external gas source. As the inert gas flows over the sharp point 146 of the blade 118 held high voltage and high frequency, a cold plasma beam is generated.

Figure 4:
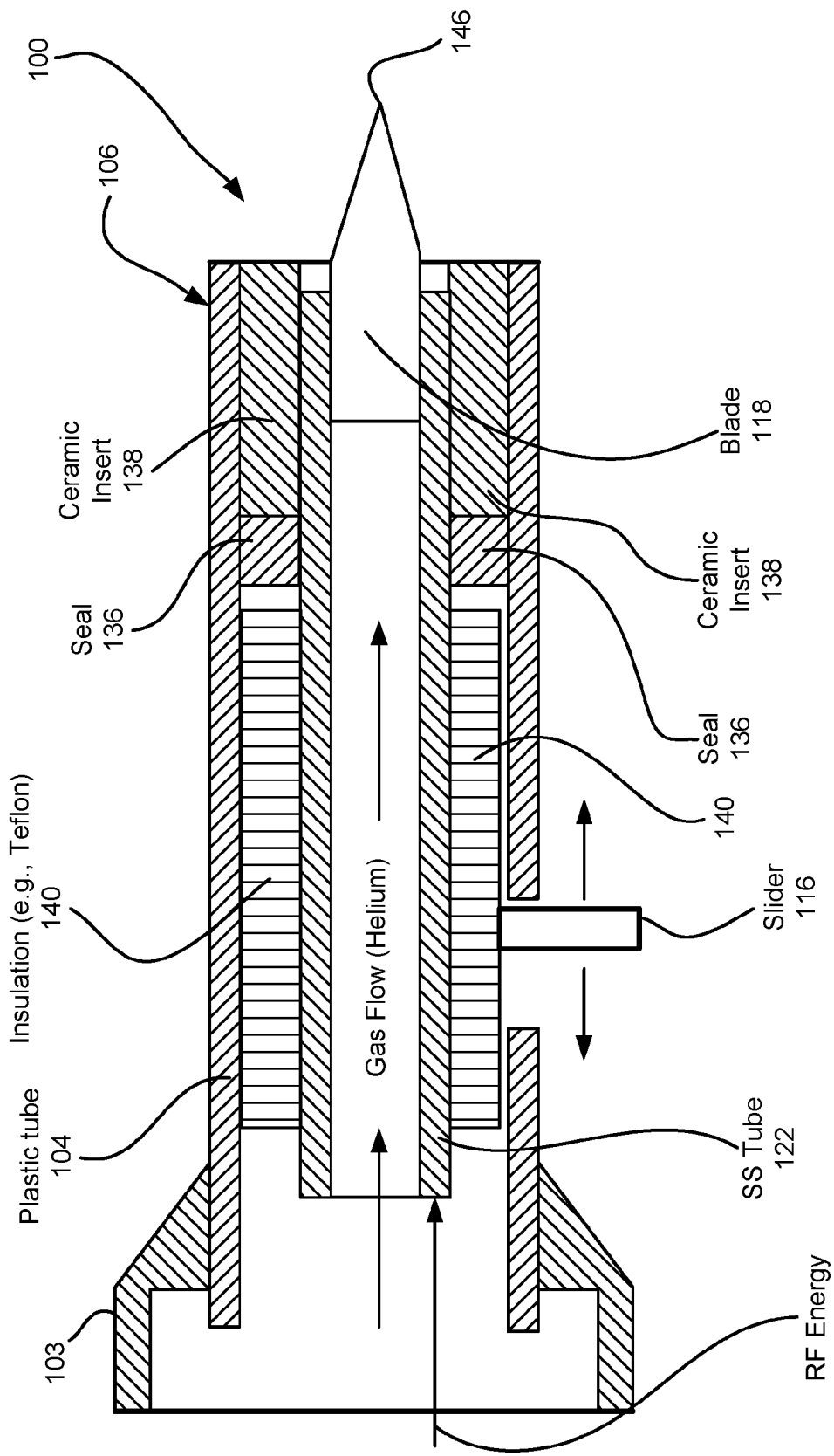
FIG. 4 is an enlarged cross sectional view of the electrosurgical apparatus shown in FIG. 3A with a blade extended.

Referring to FIG. 4, the blade 118 is advanced, via slider 116, so the tip 146 is extended past the distal end 106 of the outer tube 104. In this state, the blade 118 can be used for two cutting modes: mechanical cutting and electrosurgical cutting. In the mechanical cutting mode, RF or electrosurgical energy is not applied to the flow tube 122 or blade 118, and therefore, the blade 118 is in a de-energized state. In this mode, the blade 118 can be used excise tissue via mechanical cutting. After the tissue is removed, the blade 118 may be retracted via the slider 116 and electrosurgical energy and gas may be applied via button 114 to generate a cold plasma beam for cauterization, sterilization and/or hemostasis of the operative patient site.

In the electrosurgical cutting mode, the blade 118 is advanced and used while both electrically energized and with inert gas flow. This configuration resembles an electrosurgical knife approach, where the electrosurgical energy does the cutting. However, with the addition of the inert gas flow, cuts made show virtually no eschar, with very little collateral damage along the side walls of the cut. The cutting speed is considerably faster, with less mechanical cutting resistance as compared to when the knife blade is not electrically energized, i.e., the mechanical cutting mode. Hemostasis is also affected during this process.

Figure 5:
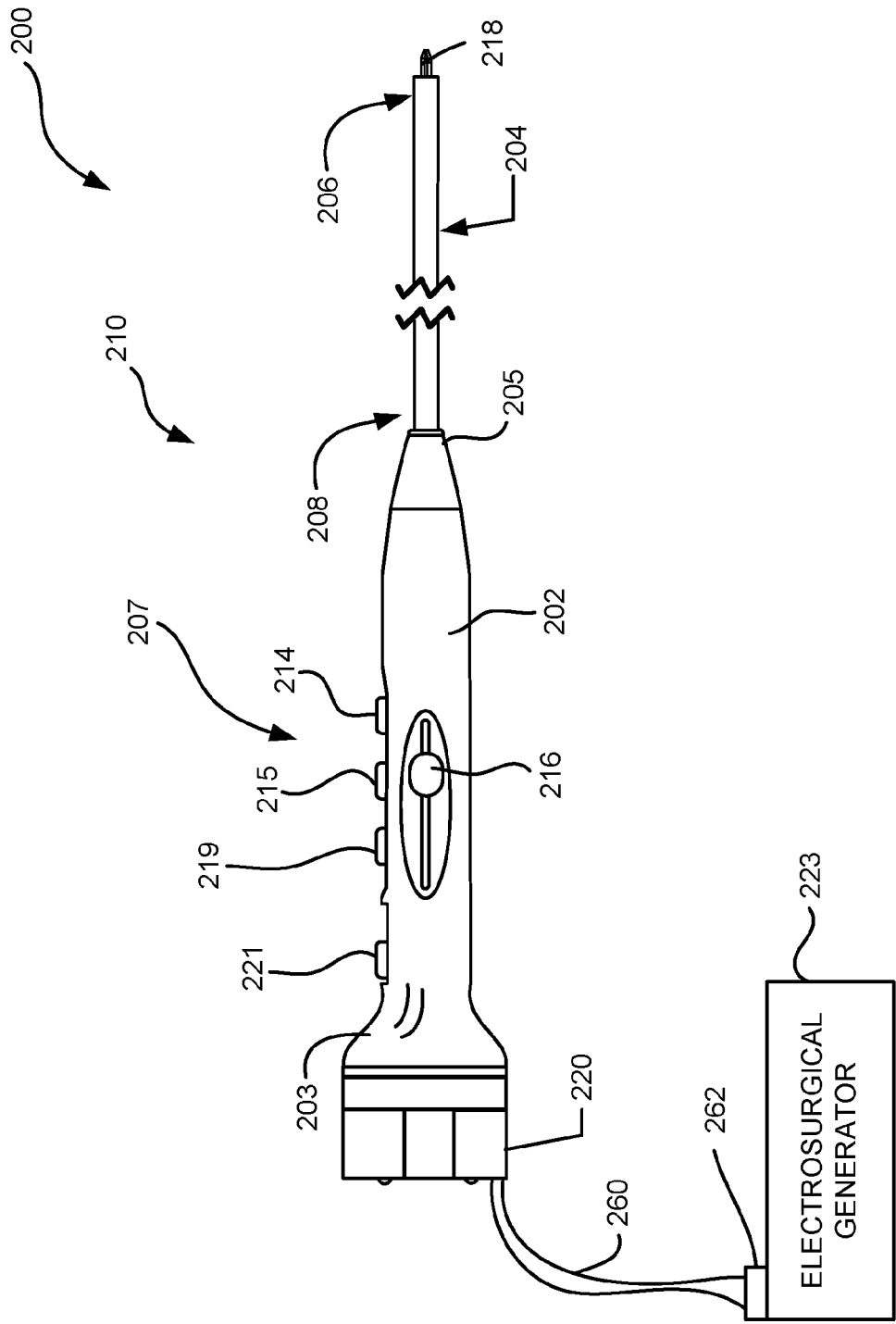
FIG. 5 illustrates an electrosurgical apparatus in accordance with another embodiment of the present disclosure.
Figure 6A:
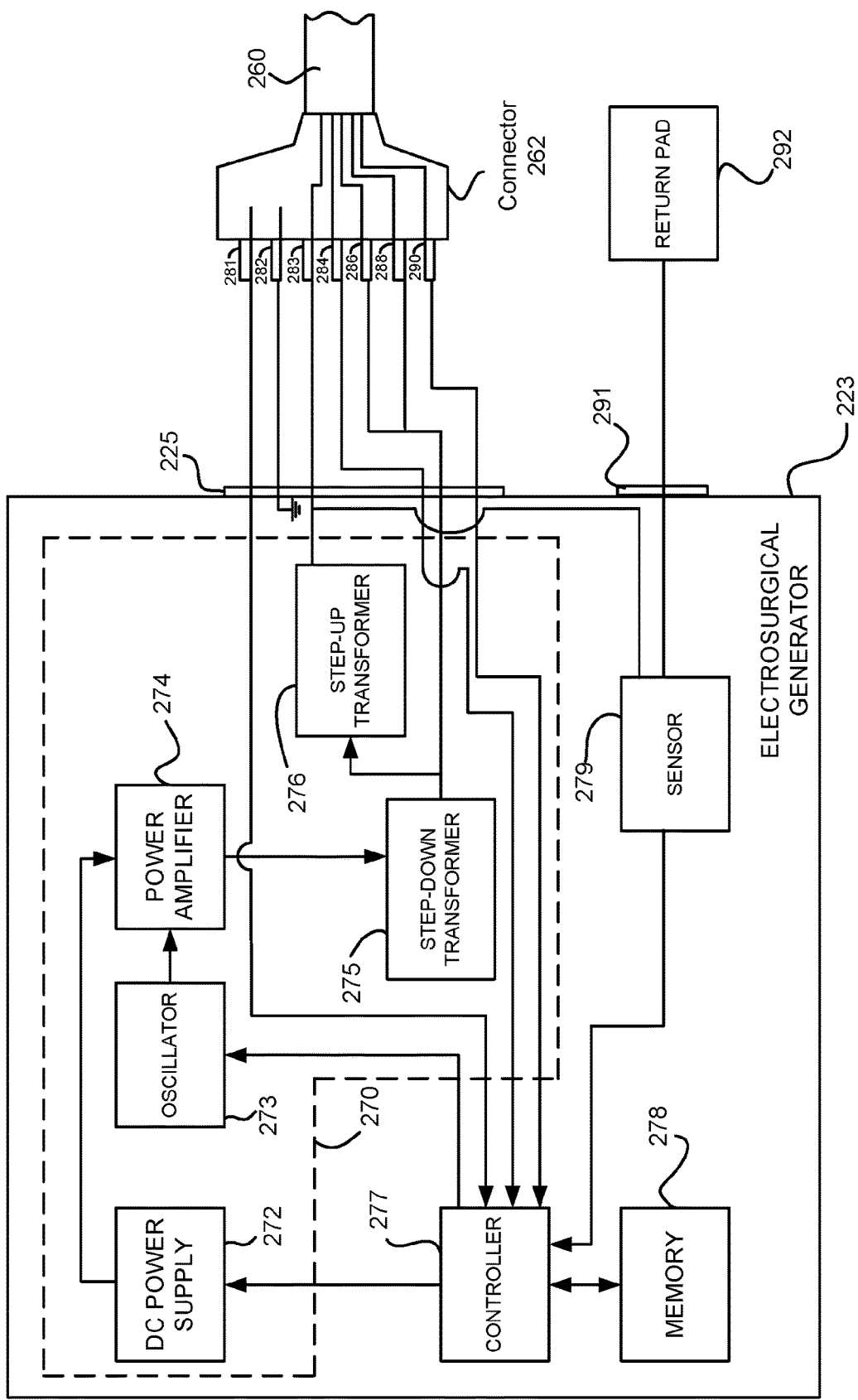
FIG. 6A is an electrical schematic diagram of an electrosurgical generator in accordance with an embodiment of the present disclosure.

Referring to FIGS. 5 and 6A, an electrosurgical apparatus 200 in accordance with another embodiment of the present disclosure is illustrated. Generally, the apparatus 200 an applicator 210 and an ESU 223. Applicator 210 includes a housing 202 having a proximal end 203 and a distal end 205 and a tube 204 having an open distal end 206 and a proximal end 208 coupled to the distal end 205 of the housing 202, thereby forming a handpiece or applicator. The housing 202 includes a plurality of buttons 207, e.g., buttons 214, 215 and 219, and a first slider 216 and second slider 221. Activation of the first slider 216 will expose a blade 218 at the open distal end 206 of the tube 204, as described above. Activation of the second slider 221 sets the apparatus into different modes, as will be described below. Activation of the individual buttons 214, 215, 219 will apply electrosurgical energy to the blade 218 to affect different electrosurgical modes and, in certain embodiments, enable gas flow through an internal flow tube 222, as will be described in detail below. Additionally, a transformer assembly 220 is provided on the proximal end 203 of the housing 202 for coupling a source of radio frequency (RF) energy to the applicator 210 via cable 260 and connector 262. The cable 260 includes a plurality of conductors for providing electrosurgical energy to the applicator 210 and for communication signals to and from the applicator 210 and an RF source, e.g., an electrosurgical generator 223. The connector 262 includes various pins, e.g., pins 281, 282, 283, 284, 286, 288 and 290, for coupling the connector 262 to corresponding port 225 on the generator 223.

As can be seen in FIG. 6A, the electrosurgical generator 223 includes a DC power supply 272, an oscillator 273, a power amplifier 274, a step-down transformer 275 and a step-up transformer 276. Collectively, power supply 272, oscillator 273, power amplifier 274, step-down transformer 275, and step-up transformer 276 form a power generator circuit 270 for supplying power or electrosurgical energy to the applicator 210. The electrosurgical generator 223 further includes a controller 277, memory 278, and sensor 279. It is to be appreciated that, in one embodiment, controller 277 may be configured as a field programmable gate array (FPGA).

Power supply 272 is configured to supply power to power amplifier 274. Power amplifier 274 is configured to receive the supply power provided from power supply 272 and generate a power signal (i.e., electrosurgical energy to be provided to electrosurgical applicator via connector 262 and cable 260). Oscillator 273 is configured to modulate the power signal generated by power amplifier 274 at different frequencies based on the mode of operation. Power supply 272 and oscillator 273 each receive control signals from controller 277. Controller 277 is configured to provide control signals to power supply 272 to increase or decrease the power supplied to power amplifier 274, thereby increasing or decreasing the power of the electrosurgical energy outputted by electrosurgical applicator 210. Controller 277 is further configured to provide control signals to oscillator 273 to change the properties (e.g., frequency, amplitude, duty cycle, crest factor, etc.) of the waveform outputted by power amplifier 274. Controller 277 is configured to receive one or more communication signal via activation of buttons 214, 215, 219 to change the electrosurgical mode of operation (i.e., J-plasma or plasma mode, CUT mode, and COAG mode, described below) as desired by a user.

Activation of the individual buttons 214, 215, 219 will apply electrosurgical energy to the blade 218 via power generator circuit 270 to affect different electrosurgical modes depending on the position of the blade 218. In the embodiment shown, button 214 is configured for activating a J-Plasma mode, button 215 is configured for activating a COAG (or coagulation) mode and button 219 is configured for activating a regular, electrosurgical CUT mode. It is to be appreciated that J-plasma mode corresponds to modes where applicator 210 generates a plasma beam to be applied to a load. Unlike conventional electrosurgical modes of operation, J-Plasma mode employs higher nominal working impedance and higher working voltages, which are able to create a gentle plasma beam at the output of an applicator, such as applicator 210 using lower power (e.g., up to 40 W) and lower output currents than conventional electrosurgical modes of operation. J-plasma mode may be employed to produce a plasma beam both when blade 218 is retracted to support contactless procedures to coagulate or ablate tissue (e.g., in a plasma mode) and when blade 218 is extended to support cutting procedures (with gas) and pin-point coagulation of tissue. In contrast to J-Plasma mode, in other modes, such as COAG and CUT, higher power (e.g., over 40 W) is used. For example, when button 215 is pressed with blade 218 retracted, more power plasma generation occurs in COAG mode (or fulguration mode) for use in contactless applications. With the blade 218 extended, a second COAG mode is achieved, e.g., a pin-point mode. When button 214 is pressed and the blade 218 is extended, a plasma, gentle CUT mode may be employed. ESU 223 and/or applicator 210 may include one or more buttons enabling switching between monopolar and bipolar modes of operation.

It is to be appreciated that the two step-up transformers 220, 276 (i.e., transformer 220 in the applicator 210 for enabling the J-Plasma mode and transformer 276 in the generator 223 for enabling the general electrosurgery mode) have two different power curves. That is their output impedances are matched for different loading conditions. The transformer 220 in the applicator 210 will put out higher voltages than the electrosurgery transformer 276 in ESU 223, but the transformer 220 is also matched for a higher output impedance for the combined tissue load and the plasma beam impedances in series. The electrosurgery transformer 276 back in the ESU 223 has a lower output voltage, but higher current capability and its output impedance is matched to the lower impedance value of an electrosurgical blade 218 in direct contact with tissue. Exemplary values for the output in J-Plasma mode are 10 kilo ohm output impedance, 4 kV to 6 kV peak-to-peak and 140 mA, where the exemplary values for the output in electrosurgery mode (i.e., corresponding to modes other than J-plasma, such as, CUT, COAG (e.g., pin-point or fulguration), and bipolar modes) are 150-250 ohm output impedance, 300 V to 6.5 kV peak-to-peak and 1.5 Amps. It is to be appreciated these exemplary values are for illustrative purposes only and in use the values may vary.

In some embodiments, gas may be provided to the applicator 210 when in COAG/CUT mode. In one embodiment with the blade 218 extended, a mode button may be provided on the generator to enable gas to flow, e.g., CUT with gas. In another embodiment, when the blade 218 is retracted, fulguration or fulguration with gas may be enabled from a button in the ESU 223.

It is to be appreciated that, although electrode 218 is shown and described as a blade in the embodiments above, in other embodiments, electrode 218 may be configured in other shapes as desired, such as, but not limited to, a wire, needle, or ball type electrode.

Figure 6B:
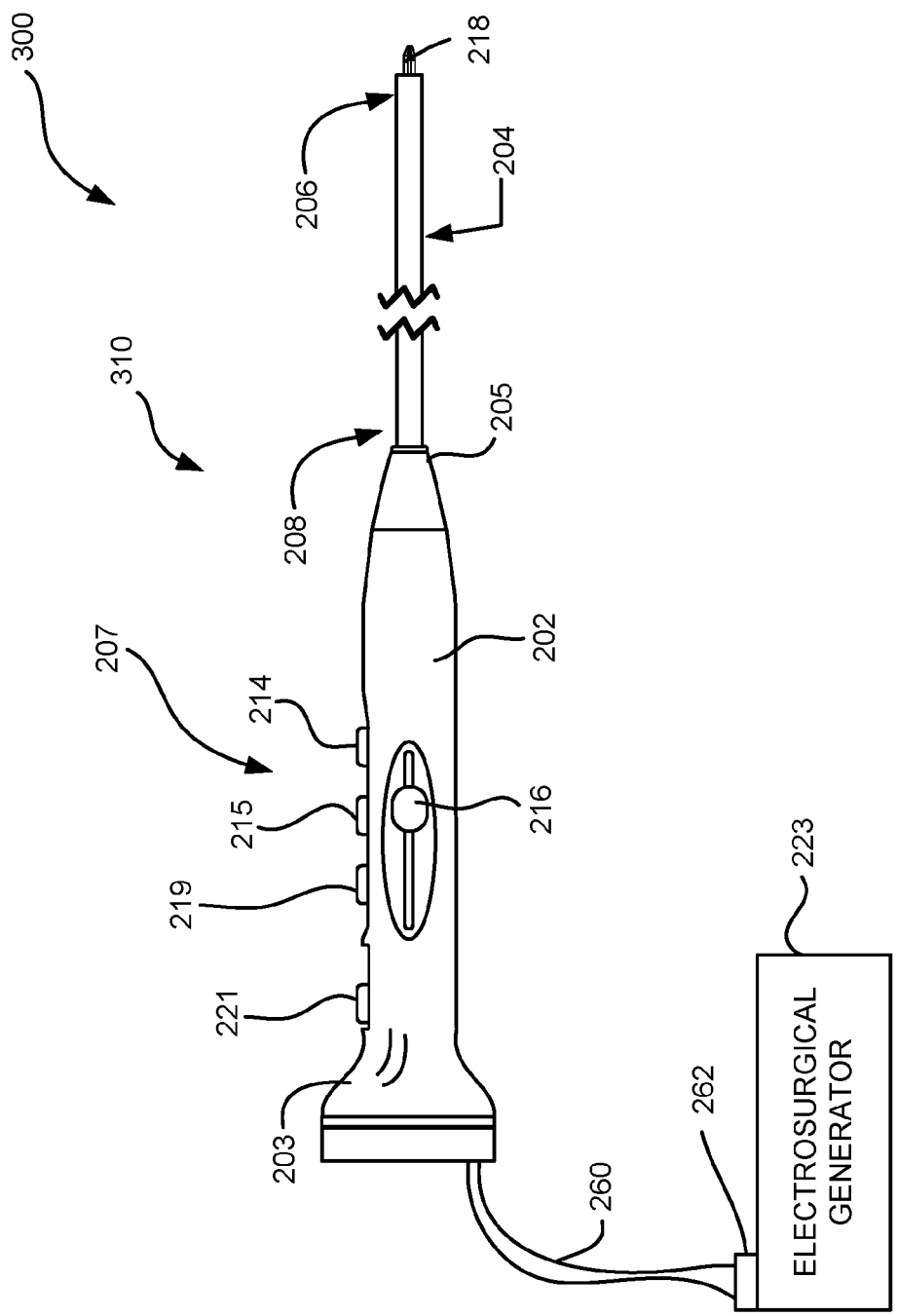
FIG. 6B illustrates another electrosurgical apparatus in accordance with another embodiment of the present disclosure.

In another embodiment of the present disclosure, ESU 223 may also be configured for use with electrosurgical applicators that do not include transformers. In one embodiment, transformer 220 of electrosurgical applicator 210 is removed. For example, referring to FIG. 6B, an electrosurgical apparatus 300 including an applicator 310 coupled to ESU 223 is shown in accordance with the present disclosure. As shown in FIG. 3, applicator 310 does not include a transformer assembly, such as, transformer assembly 220. It is to be appreciated that ESU 223 is configured for use with both applicators that include internal transformers (e.g., applicator 210) and applicators that do not include internal transformers (e.g., applicator 310).

In this embodiment, where electrosurgical applicator 310 does not include an internal transformer (i.e., where transformer 220 is not included), a new plasma mode, herein called, internal J-Plasma mode, is implemented by controller 277 of ESU 223 to enable applicator 310 to mimic J-Plasma mode despite the absence of an internal transformer in applicator 310. Internal J-Plasma mode is designed for use where an output RF transformer (e.g., transformer 276) is only disposed inside ESU 223 (rather than within the electrosurgical applicator 310). To optimize the performance of electrosurgical applicator 310 that does not include an internal transformer, the present disclosure provides two algorithms or functions.

The first algorithm or function is called dynamic leakage current compensation and is used when calculating the output current and voltage at an instrument coupled to ESU 223, such as electrosurgical applicator 310. The dynamic leakage current compensation algorithm or function of the present disclosure enables internal J-Plasma mode to work with very high RMS voltages and to mimic to the highest extent the performance of the J-Plasma mode that is used by an electrosurgical applicator 210 that includes a transformer, such as transformer 220. As will be described in greater detail below, the dynamic leakage current compensation algorithm or function of the present disclosure is advantageous when used for low power RF electrosurgical applications with flat power curves up to 20 kΩ. Such power curves would allow the user to work with very low power (e.g., down to 10 W) for minimum collateral damage on patient's tissue, and at the same time, it would provide improved performance on different tissues without electrode dragging and stickiness.

The second algorithm or function is called dynamic RF modulation and is used to dynamically control the crest factor (by adjusting modulation frequency) of the output waveform based on the measured tissue impedance when electrosurgical applicator 310 is in internal J-Plasma mode. The dynamic RF modulation algorithm or function of the present disclosure provides very high peak voltage (i.e., high crest factor) to help plasma ignition at the distal end 206 of applicator 310 when working with no load (i.e., idle), but at the same time provides much lower crest factors when cutting tissue with the electrosurgical applicator's blade (e.g., blade 218), thus helping to improve the performance of the new internal J-Plasma mode.

It is to be appreciated that both the dynamic leakage current compensation algorithm or function and the dynamic RF modulation algorithm or function may be implemented in a processor, controller, or FPGA of an electrosurgical generator, such as, controller 277 of ESU 223. Controller 277 is configured to implement the dynamic leakage current compensation algorithm by sending one or more control signals to power supply 272 to adjust the power supplied to power amplifier 274 (and thus also adjusting the power of the electrosurgical energy applied to a load by applicator 310). Controller 277 is configured to implement the dynamic RF modulation algorithm by sending one or more control signals to oscillator 273 to adjust the modulation frequency of the power signal outputted by power amplifier 274 (and thus also adjusting the modulation frequency and crest factor of the electrosurgical energy applied to a load by applicator 310). As will be described below, in some embodiments, controller 277 is configured to execute each algorithm or function concurrently.

It is to be appreciated that each algorithm or function of the present disclosure may be executed by controller 277 in hardware, software, firmware, or any combinations thereof. In some embodiments, each algorithm or function may be implemented in software or firmware that is stored on a memory device (e.g., a memory device) and that is executable by a suitable instruction execution system (e.g., a processing device, such as, controller 277). In some embodiments, the various modules (e.g., a first module corresponding the dynamic leakage current compensation algorithm or function, a second module corresponding to the dynamic RF modulation algorithm or function, etc.) of controller 277 may be implemented in hardware using, for example, discrete logic circuitry, an application specific integrated circuit (ASIC), a programmable gate array (PGA), a field programmable gate array (FPGA), or any combinations thereof.

In one embodiment, ESU 223 includes a sensor for sensing one or more electrical parameters of the terminals of ESU 223 (i.e., active and return terminals) and of a neutral electrode or return pad that is attached to a patient in monopolar applications. For example, referring again to FIG. 6A, ESU 223 may include a sensor 279 that is configured to sense one or more electrical parameters (e.g., voltage, current, etc.) of the active and return terminals of ESU 223. The active terminal of ESU 223 corresponds to the output of transformer 276 coupled to pin 283 of connector 262. The return terminal of ESU 223 corresponds to port 291. The active terminal of ESU 223 provides a power signal (i.e., electrosurgical energy) outputted from step-up transformer 276 to an electrosurgical applicator, such as applicator 310. The return terminal of ESU 223 provides a return path for the power signal outputted by the electrosurgical applicator 310 and applied to a load.

As shown in FIG. 6A, sensor 279 is coupled to controller 277. Sensor 279 is also coupled to return pad 292 via a port 291 (the return terminal of ESU 223) and to the output of transformer 276 (the active terminal of ESU 223). Sensor 279 is configured to sample the power signal at the active and return terminals of ESU 223 to sense voltage and current data. Sensor 279 is configured to transmit sensed or measured electrical parameters to controller 277. Furthermore, in one embodiment, sensor 279 may include one or more analog-to-digital converters to convert any sensed analog data to digital data that is readable by controller 277. In some embodiments, sensor 279 may include at least one current sensor to sense current and at least one potential transformer to sense voltage. It is to be appreciated that other sensors for sensing electrical parameters at the active and return terminals of ESU 223 are contemplated to be within the scope of the present disclosure.

RF Parameters

Table 1, shown below, includes the RF parameters for the output push-pull generator used for implementing the dynamic leakage current compensation and dynamic RF modular algorithms or functions. It is to be appreciated that the push-pull generator is the power amplifier stage 274 that drives the output transformers 275, 276.

TABLE 1

Internal J-Plasma mode of operation - RF parameters.
RF PARAMETERS

| Frequency of Operation | 336 kHz |
|---|---|
| Dead Time | 262.5 ns |
| Number of ON RF Pulses | 4 |
| Duty Cycle | 24 to 68% |
| Modulation Frequency | 20 to 57 kHz |

It is to be appreciated that the results shown in Table 1, and the results described below have been conducted on an ESU, such as ESU 223, using an electrosurgical applicator, such as, electrosurgical applicator 310, that is operating in internal J-Plasma mode (i.e., where applicator 310 does not include a transformer).

RF Leakage Compensation Model

When ESU 223 is working with high output voltages (e.g., above 400 Vrms) or high output currents (e.g., above 1 Arms), the impedance characteristics of the accessory cable 260 of the electrosurgical applicator 310 coupled to ESU 223 should be taken into consideration when delivering the output power. The impedance characteristics to consider include the series resistance and inductance of the wires in cable 260, the parallel stray capacitance to earth and neutral electrode 292. In the case of J-Plasma mode (e.g., where an electrosurgical applicator is used that includes an internal transformer, such as transformer assembly 220), there are high output voltages (up to 900 Vrms) and output impedances up to 20 kΩ. Furthermore, the accessory impedance value for the working RF frequency is close to or even below the output load, i.e., the measured impedance for a 2.4 m long cable at 336 kHz is between 6300Ω and 7200Ω (this measurement is with no load attached to the accessory in ground reference mode).

As the impedance of the accessory depends on the length of the cable 260 and the materials it was made of, it can be assumed that the attributes of the circuit are distributed throughout its length and material. The accessory can be represented as distributed element model where δx is small portion of the accessory length. For example, referring to FIG. 7, a distributed element model 350 of an ESU accessory, such as cable 260, is shown in accordance with the present disclosure.

Figure 7:
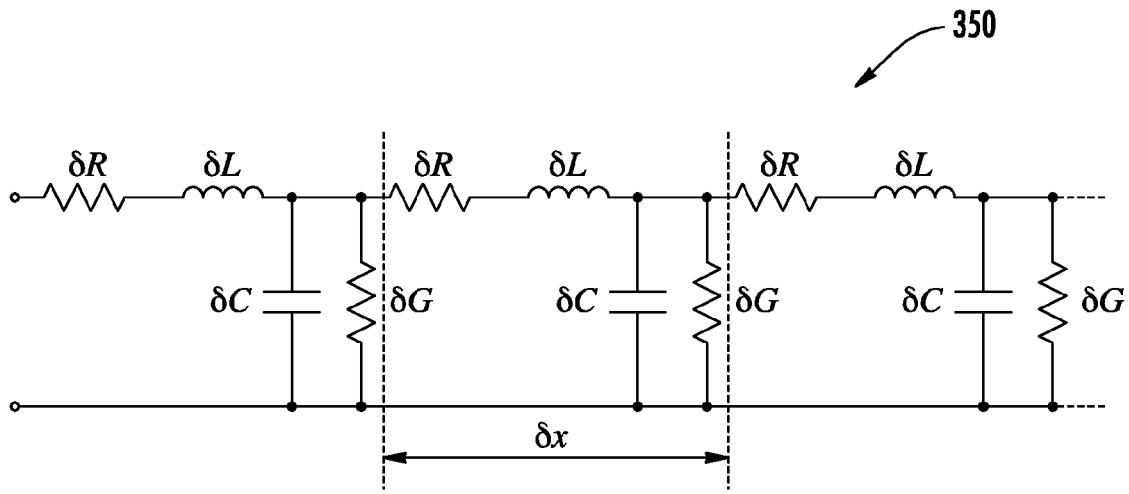
FIG. 7 is a distributed element model in accordance with an embodiment of the present disclosure.
Figure 8:
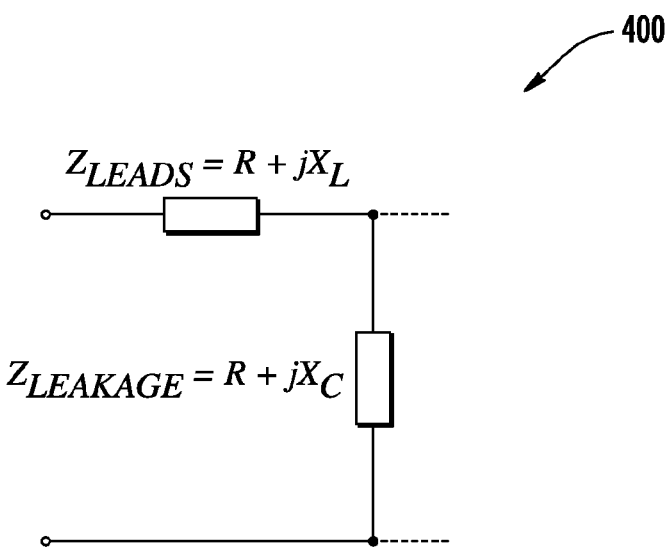
FIG. 8 is a lumped element model in accordance with an embodiment of the present disclosure.

The distributed model 350 shown in FIG. 7 is used at high frequencies where the wavelength is comparable to the dimensions of the accessory cable 260. In the case of electrosurgical working frequencies (200 kHz to 2 MHz) where the cable length is too short compared to the wavelength, this distributed element model 350 can be simplified to a lumped element circuit 400 as shown on FIG. 8, in accordance with the present disclosure. It is to be appreciated that $Z_{LEADS}$ and $Z_{LEAKAGE}$ in FIG. 8 represent the lumped impedances of the accessory, e.g., cable 260. It is assumed that $Z_{LEADS}$ is the series component and $Z_{LEAKAGE}$ the parallel component. It is to be appreciated that, in some embodiments, $Z_{LEAKAGE}$ also includes the equivalent parallel impedance of the applicator 310.

Figure 9:
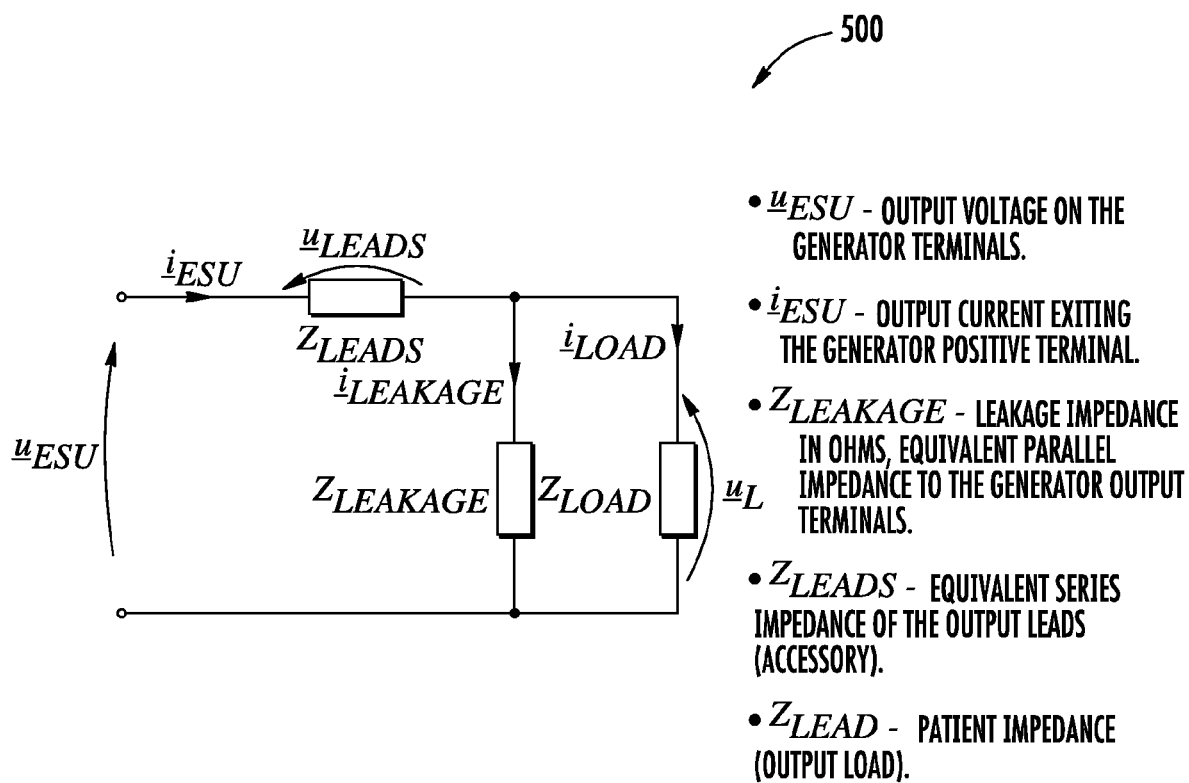
FIG. 9 is an output load circuit in accordance with an embodiment of the present disclosure.

It is to be appreciated that the lumped element model 400 shown in FIG. 8 may be used to derive a simplified ESU output circuit by adding the output load impedance (i.e., tissue impedance). It is to be appreciated that in an electrosurgical application, $Z_{LOAD}$ is the tissue impedance. In J-Plasma mode, $Z_{LOAD}$ is the combined impedance of the plasma beam and the tissue impedance. For example, referring to FIG. 9, output load circuit 500 is shown in accordance with the present disclosure. FIG. 9 includes $\underline{u}_{ESU}$, $i_{ESU}$, $Z_{LEAKAGE}$, $Z_{LEADS}$, and $Z_{LOAD}$, where $\underline{u}_{ESU}$ is the output voltage across the active and return terminals of ESU 223, $i_{ESI}$ is the output current exiting through the active terminal of ESU 223, $Z_{LEAKAGE}$ is the leakage impedance, in ohms, equivalent parallel impedance to the ESU 223 active and return terminals, $Z_{LEADS}$ is the equivalent series impedance of the output leads (e.g., of an accessory, such as cable 260) and $Z_{LOAD}$ is the patient impedance (i.e., output load).

Based on the output load circuit 500, the following equations are derived:

$$i_{LEAKAGE} = \frac{u_{ESU} - u_{LEADS}}{Z_{LEAKAGE}} \quad (1)$$

$$i_{LOAD} = i_{ESU} - i_{LEAKAGE} \quad (2)$$

$$u_{LEADS} = i_{ESU} \times Z_{LEADS} \quad (3)$$

$$u_{LOAD} = u_{ESU} - u_{LEADS} \quad (4)$$

It is to be appreciated that the dynamic leakage current compensation algorithm or function of the present disclosure (executed by FPGA or controller 277) may implement a further simplification by making certain assumptions. In one embodiment, it is assumed that the two types of compensations (i.e., leakage and leads) have a small or negligible impact on each other. In other words, when there is high current and low output impedance, the leakage correction will be negligible. Throughout the working range of the ESU 223, it is assumed that either leakage compensation is dominant or leads compensation is dominant. With this assumption, equation 1 (shown above) is modified to:

$$i_{LEAKAGE} = \frac{u_{ESU}}{Z_{LEAKAGE}} \quad (5)$$

The modification of equation 5 above makes the logic for the dynamic leakage current compensation algorithm or function of the present disclosure more straightforward.

Figure 10:
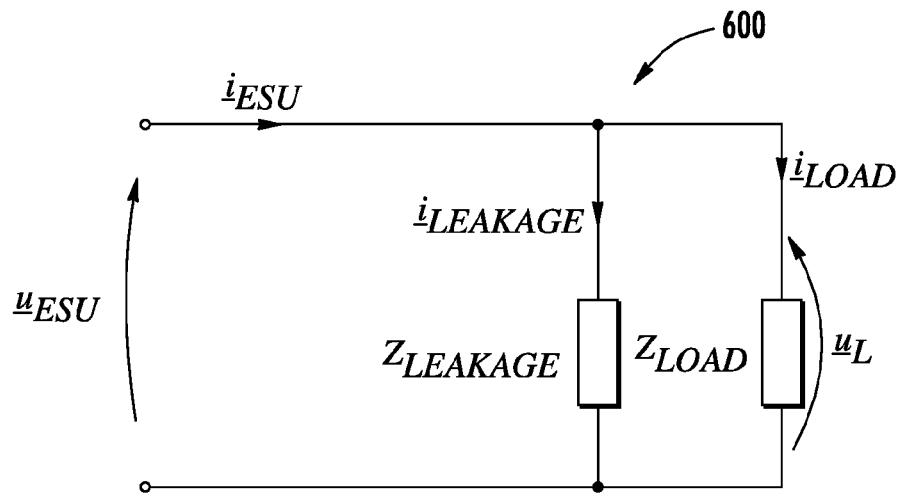
FIG. 10 is an equivalent load circuit for performing leakage compensation in accordance with an embodiment of the present disclosure.

Referring to FIG. 10, equivalent load circuit 600 is shown in accordance with the present disclosure, where circuit 600 is used to measure the load current when performing leakage compensation.

The internal J-Plasma mode requires very high working voltages (e.g., up to 900 $V_{RMS}$) and flat power curve up to 20 kΩ. However, above 400 $V_{RMS}$, the electrical model of the equivalent load circuit 600 becomes more and more inaccurate with the increase of the output voltage. As the output voltage increases, the leakage current also increases due to other leakage losses not included in the electrical model of circuit 600. This may decrease the performance of the internal J-Plasma mode when working at higher impedances and may worsen the flatness of the power curve.

Figure 11:
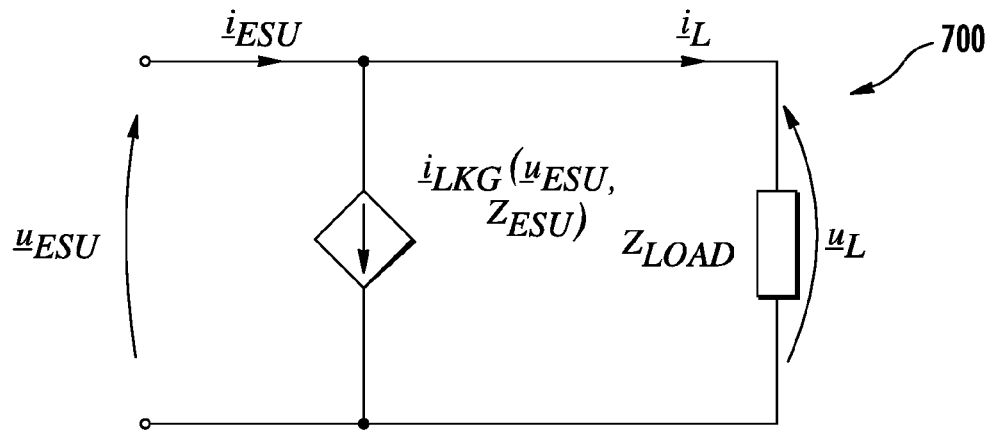
FIG. 11 is an equivalent electrical model of the circuit shown in FIG. 10 in accordance with an embodiment of the present disclosure.

To compensate for the above described inaccuracies of the model of circuit 600 when working at higher voltages, a new model is provided. Referring to FIG. 11, a circuit 700 is shown in accordance with the present disclosure. Circuit 700 is an equivalent electrical model of the ESU output load circuit 600 shown in FIG. 10. In circuit 700, the leakage impedance ($Z_{LEAKAGE}$) is replaced with controlled current source ($i_{LKG}$) which is a function of the ESU output voltage ($\underline{u}_{ESU}$) and sensed (e.g., by sensor 279) ESU impedance ($Z_{ESU}$).

It is assumed that the leakage impedance ($Z_{LEAKAGE}$) is decreasing with the increase of the output voltage as the leakage current is higher. It is also assumed that the leakage current will have greater impact on the output power when working at higher output loads. This justifies the substitution of the leakage impedance with the controlled current source in circuit 700 of FIG. 11, which depends on the output voltage and impedance. The equation of the current control source is given by the formula below:

$$i_{LKG} = f(u_{ESU}, Z_{ESU}) = \frac{u_{ESU}}{Z_{LEAKAGE}(Z_{ESU})} \quad (6)$$

where $Z_{LEAKAGE}$ is a function of $Z_{ESU}$. If $Z_{ESU}$ is increasing, $Z_{LEAKAGE}$ is decreasing.

It is to be appreciated that the function $Z_{LEAKAGE}=f(Z_{ESU})$ is derived by approximation. Experimentally, the leakage impedance can be measured with the internal J-Plasma mode instrument for a set of output loads (e.g., 20 kΩ, 15 kΩ, 10 kΩ, 5 kΩ etc.). As the leakage impedance ($Z_{LEAKAGE}$) is assumed parallel to the output load, the following equation is derived:

$$Z_{ESU} = \frac{Z_{LEAKAGE} \times Z_{LOAD}}{Z_{LEAKAGE} + Z_{LOAD}} \quad (7)$$

and the leakage impedance is:

$$Z_{LEAKAGE} = \frac{Z_{LOAD} \times Z_{ESU}}{Z_{LOAD} + Z_{ESU}} \quad (8)$$

Based on equations (2) and (6), shown above, the output current is derived by:

$$i_{LOAD} = i_{ESU} - \frac{u_{ESU}}{Z_{LEAKAGE}(Z_{ESU})} \quad (9)$$

Dynamic Leakage Compensation

Figure 12A:
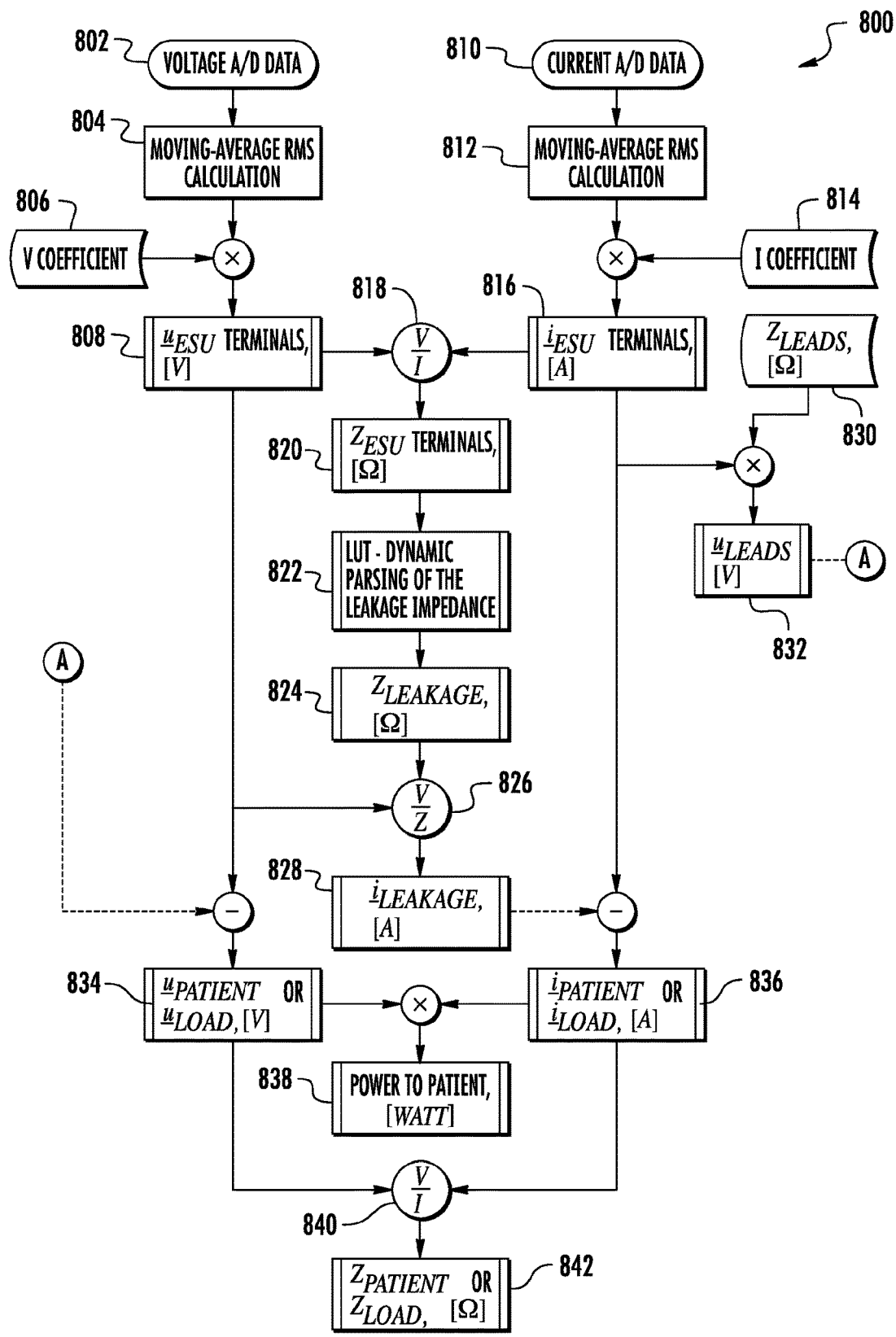
FIG. 12A is a flow chart of a dynamic leakage current compensation algorithm or function in accordance with an embodiment of the present disclosure.

Referring to FIG. 12A, the dynamic leakage current compensation algorithm or function is shown as method 800 in accordance with the present disclosure. It is to be appreciated that, in one embodiment, the dynamic leakage current compensation algorithm or function may be executed by controller 277 to control the power outputted by power supply 272 and thus the power of the electrosurgical energy provided to the patient or load. Furthermore, it is to be appreciated that, in one embodiment, controller 277 executes the steps of method 800 in parallel on each positive edge of the system clock inside controller 277.

In step 802 and 810, sensor 279 concurrently samples voltage data and current data at the active terminal and the return terminal of ESU 223, where the sampled voltage and current data is associated with the electrosurgical energy provided via power generator circuit 270 to applicator 310. For example, sensor 279 may sample output voltage across the active and return terminals of ESU 223 and the output current of step-up transformer 276 at the active terminal of ESU 223. It is to be appreciated that, in one embodiment, sensor 279 includes parallel analog-to-digital converters for converting the analog samples of the voltage and current to digital data, where the voltage and current data is then provided to controller 277. Controller 277 then uses the voltage data to calculate a moving-average RMS for the voltage data, in step 804, and the current data to calculate a moving-average RMS for the current data, in step 812. It is to be appreciated that, in one embodiment, the output of the moving-average RMS calculation in steps 804 and 812 may include an RMS value for the last 4096 sampling points, sampled by sensor 279.

Then, the moving-average RMS for the voltage data (calculated in step 804) is scaled by controller 277 by multiplying the moving-average RMS for the voltage data by a voltage scaling coefficient, in step 806, to obtain the RMS voltage across the ESU 223 terminals ($\mu_{ESU}$), in step 808. The moving-average RMS for the current data (calculated in step 812) is scaled by controller 277 by multiplying the moving-average RMS for the current data by a current scaling coefficient, in step 814, to obtain the RMS current outputted by transformer 276 and flowing from the active terminal of ESU 223 ($i_{ESU}$) towards the load (i.e., the patient's tissue), in step 816. It is to be appreciated that the voltage and current coefficients may be stored in a memory of ESU 223, such as memory 278. In one embodiment, the voltage coefficient is 6.25 mA/LSB (where LSB represents the least significant bit of the sampled current data) and the current coefficient is 9.1 V/LSB (where LSB represents the least significant bit of the sampled voltage data). In one embodiment, the voltage and current coefficients are determined based on the hardware components of ESU 223, such as, the components of sensor 279.

In step 818, controller 277 divides the RMS voltage across the active and returns terminals of ESU 223 ($\mu_{ESU}$) by the RMS current outputted by transformer 276. The output of step 818 gives the impedance across the active and return terminals of ESU 223 ($Z_{ESU}$), in step 820.

In one embodiment, memory 278 of ESU 223 may include a first lookup table (LUT) including an approximation of measured leakage impedances ($Z_{LEAKAGE}$) as a function of the impedance across the terminals of ESU 223 ($Z_{ESU}$). The first LUT includes leakage impedance values corresponding to values for the impedance across the terminals of ESU 223 ($Z_{ESU}$). It is to be appreciated that the measured leakage impedances in the first LUT may be measured values or alternatively calculated values using equation (8) above. For example, in one embodiment, the values in the first LUT are determined by measuring the impedance across the terminals of ESU 223 ($Z_{ESU}$) while applicator 310 is being used to provide electrosurgical energy under varying, known loading conditions (i.e., known load impedances $Z_{LOAD}$). With the measured $Z_{ESU}$ and the known $Z_{LOAD}$, the leakage impedance ($Z_{LEAKAGE}$) is calculated and stored in the first LUT. This is repeated for varying load impedances ($Z_{LOAD}$) until the first LUT is populated with leakage impedance ($Z_{LEAKAGE}$) values corresponding to different values for the measured impedance across the terminals of ESU 223 ($Z_{ESU}$). By using the first LUT table, the computational strain on controller 277 is reduced and the leakage impedance ($Z_{LEAKAGE}$) can be determined by controller 277 instantly.

In other embodiments, controller 277 is configured to determine the leakage impedance ($Z_{LEAKAGE}$) dynamically without the usage of the first LUT by using an equation approximating the leakage impedance ($Z_{LEAKAGE}$) as a function of the impedance across the terminals of ESU ($Z_{ESU}$).

In this embodiment, controller 277 looks up the calculated impedance across the terminals of ESU 223 ($Z_{ESU}$) in the first LUT, in step 822, to find the leakage impedance ($Z_{LEAKAGE}$) for the electrosurgical applicator 310 corresponding to the calculated impedance across the active and return terminals of ESU 223 ($Z_{ESU}$). As stated above, the leakage impedance ($Z_{LEAKAGE}$) for the electrosurgical applicator 310 is the equivalent leakage impedance of the electrosurgical applicator 310 and any accessory (e.g., cable 260) used to couple electrosurgical applicator 310 to ESU 223. In this way, controller 227 dynamically derives the leakage impedance ($Z_{LEAKAGE}$) for the electrosurgical applicator 310 that is in internal J-Plasma mode, in step 824.

In step 826, controller 277 divides the RMS voltage across the active and return terminals of ESU 223 ($\mu_{ESU}$) by the leakage impedance ($Z_{LEAKAGE}$). The output of step 826 gives the leakage current ($i_{LEAKAGE}$) of the electrosurgical applicator 310, in step 828. As stated above, the leakage current ($i_{LEAKAGE}$) of the electrosurgical applicator 310 is the leakage current ($i_{LEAKAGE}$) due electrosurgical applicator 310 and any accessory (e.g., cable 260) used to coupled electrosurgical applicator 310 to ESU 223.

In step 830, controller 277 retrieves the impedance of the output leads $Z_{LEADS}$ from memory 278. It is to be appreciated that, in one embodiment, ZLEADS, is determined empirically using a cable 260 of predetermined length. Then, controller 277 uses the RMS current outputted from transformer 276 and flowing from the active terminal of ESU 223 ($i_{ESU}$) towards the load to calculate voltage of the output leads ($\mu_{LEADS}$), in step 832. It is to be appreciated that the voltage of the output leads ($\mu_{LEADS}$) is the equivalent voltage over the length of cable 260 and is calculated in step 832 using equation (3), shown above.

The voltage across the active and return terminals ($\mu_{ESU}$), from step 808, and voltage of the output leads ($\mu_{LEADS}$), from step 832, is used by controller 277 to calculate the voltage currently being applied to the load ($\mu_{LOAD}$), in step 834. Also, the leakage current ($i_{LEAKAGE}$) of the electrosurgical applicator 310, from step 828, and the RMS current flowing from the active terminal of ESU 223 ($i_{ESU}$) towards the load, from step 816, is used by controller 277 to calculate the output current currently being applied to the load ($i_{LOAD}$), in step 836. It is to be appreciated that the voltage currently being applied to the load ($\mu_{LOAD}$) may be calculated by controller 277 using equation (4) and the output current currently being applied to the load ($i_{LOAD}$) may be calculated by controller 277 using equation (9), shown above.

The voltage currently being applied to the load ($u_{LOAD}$) and the output current currently being applied to the load ($i_{LOAD}$) is then used by controller 277 to calculate the output power currently being applied to the load by applicator 310, in step 838. Also, the voltage currently being applied to the load ($u_{LOAD}$) is divided by the output current currently being applied to the load ($i_{LOAD}$) by controller 277, in step 840, to calculate the impedance ($Z_{LOAD}$) of the load, in step 842. The impedance of the load ($Z_{LOAD}$) calculated in step 840 may be stored in a memory 278 of ESU 223 by controller 277 to be used as diagnostic data to check how different the patient or load calculated impedance ($Z_{LOAD}$) is compared to the impedance sensed ($Z_{ESU}$) by ESU 223.

It is to be appreciated the dynamic leakage current compensation algorithm or function of method 800 may be executed by controller 277 of ESU 223 continuously to dynamically adjust the power delivered to a patient or load to compensate for the leakage current calculated in step 838 of method 800.

Figure 12B:
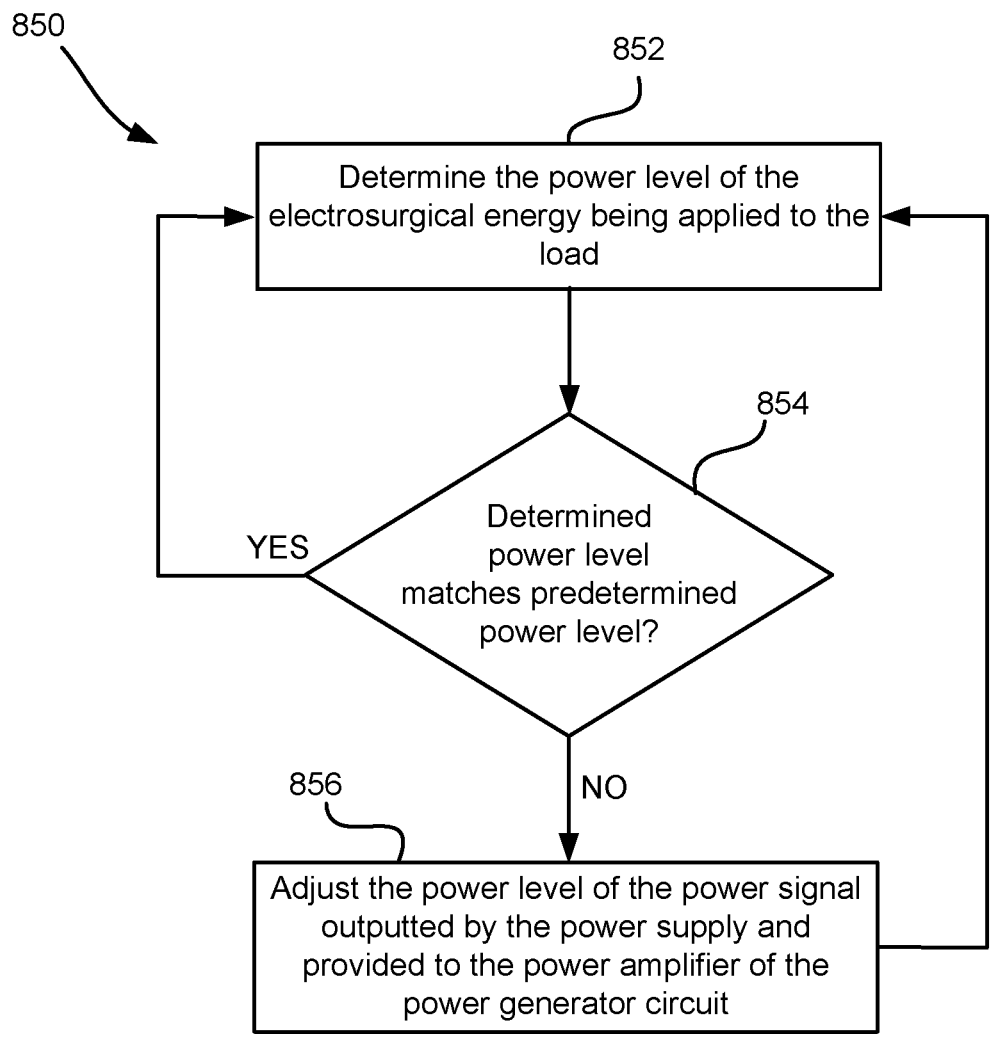
FIG. 12B is a flow chart of a method for adjusting the power being delivered to a load based on the dynamic leakage current compensation algorithm or function of FIG. 12A in accordance with an embodiment of the present disclosure.

For example, referring to FIG. 12B, a flow chart of a method 850 for adjusting the power level of the electrosurgical energy currently being applied to a patient or load based on the dynamic leakage current compensation algorithm or function of method 800 is shown in accordance with the present disclosure. In step 852, controller 277 determines the power level of the electrosurgical energy currently being applied to the patient or load by applicator 310 based on the leakage current ($i_{LEAKAGE}$). It is to be appreciated that controller 277 determines the power level of the electrosurgical energy currently being applied to the load in the manner described above in relation to step 838 of method 800. In step 854, controller 277 determines if the power level of the electrosurgical energy currently being applied to the load matches a predetermined power level, where the predetermined power level is a goal or set-point power level (selectable by a user using ESU 223) that is desired to be used in a particular procedure. The predetermined power level may be stored in memory 278.

If controller 277 determines that the power level of the electrosurgical energy currently being applied to the load matches the predetermined power level (or is within a predetermined range of the predetermined power level), in step 854, method 850 returns to step 852. Alternatively, if controller 277 determines that the power level of the electrosurgical energy currently being applied to the load does not match the predetermined power level (i.e., the currently provided power is below the predetermined power level due to the leakage current ($i_{LEAKAGE}$) of the electrosurgical applicator 310), in step 854, controller 277 is configured to adjust the power level of the power signal outputted by power supply 272 and provided to power amplifier 274 of power generator circuit 270 based on the determined power level of the electrosurgical energy being applied to the load, in step 856. It is to be appreciated that controller 277 adjusts the power level of the power signal outputted by power supply 272 by sending a control signal to the power supply 272 to increase or decrease the power level of the power signal outputted by power supply 272 as necessary to match the predetermined power level. When controller 277 causes power supply 272 to increase the power level of the power signal outputted, the power level of the electrosurgical energy applied to the patient or load is also increased (and vice versa). After step 856, the method 850 is executed again by controller 277. In this way, the power level of the electrosurgical energy applied to the load by applicator 310 is continuously and dynamically adjusted by controller 277 based on the actual power being delivered to the load (as determined in steps 838/852) to compensate for the leakage current ($i_{LEAKAGE}$) of the electrosurgical applicator 310 and to maintain a predetermined power level desired for a particular procedure.

In one embodiment, methods 800, 850 are executed by controller 277 periodically with a time interval of 400 us (e.g., 2.44 kHz frequency).

Dynamic RF Modulation

The controller 277 of ESU 223 may also be configured to execute the dynamic RF modulation algorithm or function of the present disclosure to control the RF push-pull driver or oscillator 273 in ESU 223 to provide a power signal or electrosurgical energy to the load or patient having a desired crest factor. The dynamic RF modulation algorithm or function is configured to enable controller 277 to control several parameters of the RF output of an electrosurgical applicator, such as applicator 310. The parameters include:

Frequency (1/Period)
Dead time between the push-pull pulses*
Number of RF pulses in one modulation cycle (NumberOfPulses)
Off time between each modulation cycle (OffTime)

It is to be appreciated that dead time in oscillator 273 is the time, introduced between the corresponding driving pulses of both legs of power amplifier 274 to prevent overlapping.

For the internal J-Plasma mode, each the above-listed parameters are shown in Table 1 above. It is to be appreciated that frequency of operation, dead time, and number of RF pulses are fixed. The values associated with each of frequency, dead time, and number of RF pulse in one modulation cycle are each stored in memory 278 of ESU 223. However, the dynamic RF modulation algorithm or function may be used by controller 277 to dynamically change the OffTime between each modulation cycle based on the ESU impedance ($Z_{ESU}$) from step 820 of the dynamic leakage current compensation algorithm or function shown in method 800. In other words, the OffTime between the modulation cycles is a function of the $Z_{ESU}$.

Figure 13:
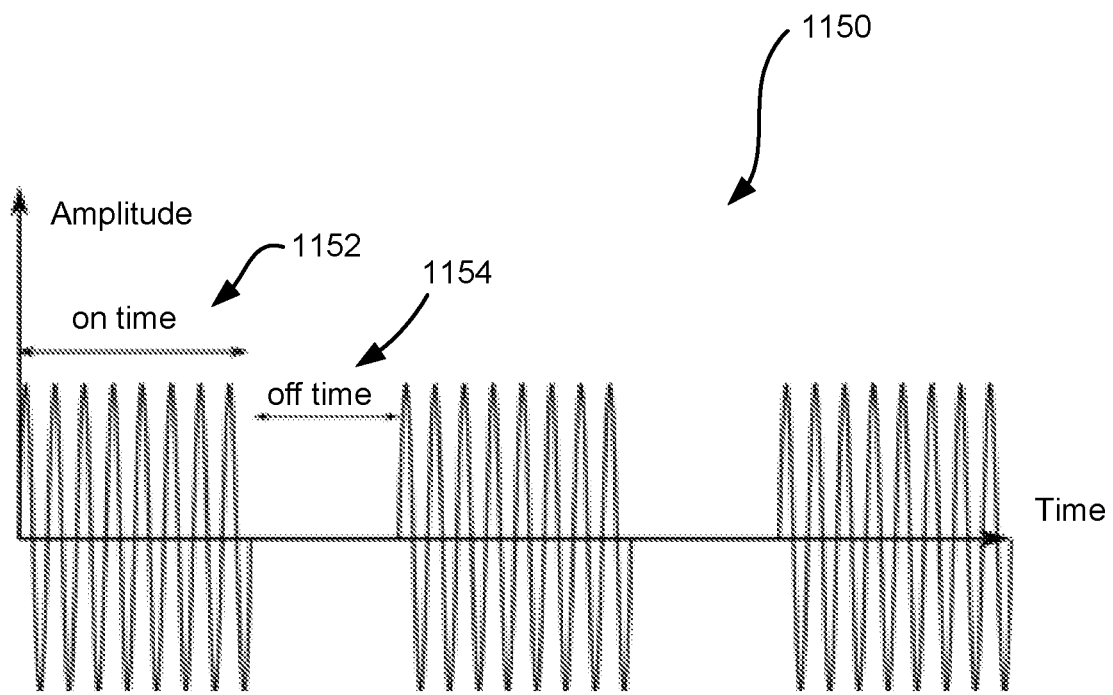
FIG. 13 is a waveform of a modulated power signal in accordance with an embodiment of the present disclosure.

Referring to FIG. 13, an exemplary modulated power signal 1150 is shown in accordance with the present disclosure. The power signal outputted by power amplifier 274 is modulated by oscillator 273. Signal 1150 of FIG. 13 is an exemplary modulated power signal outputted by power amplifier 274. The modulated power signal 1150 has an on time or oscillation cycle 1152, where the signal is modulated, as shown in FIG. 13. The modulated power signal 1150 also includes an off time 1154, where the signal is inactive (i.e., not modulated). The sum of the on time 1152 and the off time 1154 comprise a modulation cycle or period for the modulated signal 1150.

With the increase of the impedance across the active and return terminals of ESU 223 ($Z_{ESU}$), the OffTime is increasing and vice versa. As can be seen from the equations (10) and (11) below, if the OffTime is increased, the modulation frequency (i.e., the frequency of the on time 1152 plus the off time 1154) and the duty cycle are decreasing. Furthermore, the crest factor ($V_{PEAK}/V_{RMS}$) of the power signal or electrosurgical energy provided to the load will be increased, which will give higher peak voltages if the closed loop system of ESU 223 preserves the output RMS power or voltage. It is to be appreciated that the RMS power is preserved or held relatively constant by executed the leakage current compensation algorithm or function described above. Also, if the output impedance is relatively low (up to 2000Ω), the dynamic RF modulation algorithm or function will cause the controller 277 to set a lower OffTime, which will increase the duty cycle. In this manner, the cutting tissue effect will become stronger with less charring. Below, equations for modulation frequency and duty cycle are provided:

$$ModulationFrequency = \frac{1}{Period \times NumberOfPulses + OffTime} \quad (10)$$

$$DutyCycle = \frac{Period \times NumberOfPulses}{Period \times NumberOfPulses + OffTime} \quad (11)$$

In one embodiment, memory 278 includes a second LUT that includes OffTime values as a function of, and corresponding to, different values for $Z_{ESU}$. The second LUT including the values for OffTime is used in the dynamic RF modulation algorithm or function by controller 277 to determine a desired OffTime based on a determined $Z_{ESU}$ (i.e., as determined in step 820 of method 800). It is to be appreciated that the desired OffTime is an OffTime that is associated with a desired crest factor for a procedure being performed, as described below.

The OffTime is then used by controller 277 to determine a desired ModulationFrequency based on the determined $Z_{ESU}$. Controller 277 then sends a control signal to oscillator 273 to cause the power signal outputted by power amplifier 274 to have the desired ModulationFrequency based on the determined $Z_{ESU}$. In this way, as $Z_{ESU}$ varies (due to the impedance of the load $Z_{LOAD}$ varying in different loading conditions), the ModulationFrequency is adjusted, thus also adjusting the crest factor of the power signal or electrosurgical energy applied to the load.

The values in the second LUT including the OffTimes are chosen, such that, for low load impedances ($Z_{LOAD}$) the crest factor is also low to support contact/cut modes of operation of applicator 310 and for high load impedances ($Z_{LOAD}$) the crest factor is also high to support contactless modes of operation. In one embodiment, the second LUT is separated into three portions, described below.

In a first portion of the second LUT, the second LUT includes $Z_{ESU}$ and corresponding OffTime values that are associated with loading conditions where the applicator 310 is being used in a contact procedure (e.g., to cut tissue). The $Z_{ESU}$ values in the first portion are at or below a first threshold value (e.g., at or below 1.6 kΩ $Z_{ESU}$ values, which are associated with load impedances up to a 2 kΩ $Z_{LOAD}$). In the first portion of the second LUT, the corresponding OffTime values for $Z_{ESU}$, while $Z_{ESU}$ is at or below the first threshold value are selected, such that, an optimal crest factor (e.g., 2.0-2.3) for contact procedures is achieved for the electrosurgical energy outputted by power amplifier 274 when the ModulationFrequency is determined based on the OffTime in the first portion of the second LUT. In one embodiment, the OffTime values in the first portion of the second LUT are selected, such that, the crest factor of the electrosurgical energy outputted by power amplifier 274 when the second LUT is used remains relatively constant at a first predetermined value or within a first range (e.g., 2.0-2.3).

In a second portion of the second LUT, the second LUT includes $Z_{ESU}$ and corresponding OffTime values that are associated with loading conditions where the applicator 310 is being used in a contactless procedure (e.g., in a plasma mode to coagulate tissue). The $Z_{ESU}$ values in the second portion are at or above a second threshold value (e.g., at or above 3.5 kΩ $Z_{ESU}$ values, which are associated with load impedances up to a 4.5 kΩ $Z_{LOAD}$). It is to be appreciated that the second threshold value is above the first threshold value. In the second portion of the second LUT, the corresponding OffTime values for $Z_{ESU}$, while $Z_{ESU}$ is at or above the second threshold value are selected, such that, an optimal crest factor (e.g., 5.0-6.0) for contactless procedures is achieved for the electrosurgical energy outputted by power amplifier 274 when the ModulationFrequency is determined based on the OffTime in the second portion of the second LUT. In one embodiment, the OffTime values in the second portion of the second LUT are selected, such that, the crest factor of the electrosurgical energy outputted by power amplifier 274 when the second LUT is used remains relatively constant at a second predetermined value or within a second range (e.g., 5.0-6.0).

The third portion of the LUT includes $Z_{ESU}$ and corresponding OffTime values for values of $Z_{ESU}$ above the first predetermined threshold and below the second predetermined threshold (e.g., $Z_{ESU}$ values above 1.6 kΩ and below 3.5 kΩ). In this transitional range for values of $Z_{ESU}$ above the first predetermined threshold and below the second predetermined threshold, the OffTime values are selected, such that, as $Z_{ESU}$ increases in the transitional range, the crest factor of the electrosurgical energy outputted by power amplifier 274 when the second LUT is used is also increased in a relatively proportional manner. In one embodiment, the OffTime values are selected, such that, the crest factor increases in a relatively linear manner as $Z_{ESU}$ is increased. By selecting the OffTime values, such that, the crest factor is gradually increased as $Z_{ESU}$ is increased, the instability or undesired oscillations in the plasma beam outputted by applicator 310 are reduced throughout the transitional range.

By using the second LUT table, the computational strain on controller 277 is reduced and the OffTime can be determined by controller 277 instantly. In other embodiments, controller 277 is configured to determine the OffTime dynamically without the usage of the second LUT by using an equation approximating the OffTime as a function of the impedance across the terminals of ESU ($Z_{ESU}$).

In one embodiment, the OffTime values in the LUT each include minimums and maximums that represent ModulationFrequency limits from 26 to 57 kHz or the duty cycle limits from 31 to 68%. In this way, the ModulationFrequency is varying from 26 to 57 kHz and the duty cycle is within 31 to 68%.

Referring to FIGS. 14 and 15, graphs 900 and 1000 are shown in accordance with the present disclosure. Graph 900 illustrates measurements of the electrosurgical energy delivered to a load by an applicator 310 coupled to ESU 223 taken at 20 kΩ output load, where the waveform has a predominant coagulation effect (e.g., 31% duty cycle). Graph 1000 illustrates measurements taken after the output load has been changed to 1000Ω. The measurement on graph 1000 show that the waveform has a predominant cutting effect (e.g., 68% duty cycle). It is to be appreciated that graphs 900 and 1000 illustrate how modulation frequency, off time, duty cycle, and crest factor self-adjust based on different load conditions (i.e., varying load impedance $Z_{LOAD}$ and varying ESU impedance $Z_{ESU}$) using the dynamic RF modulation algorithm or function of the present disclosure.

Figure 16:
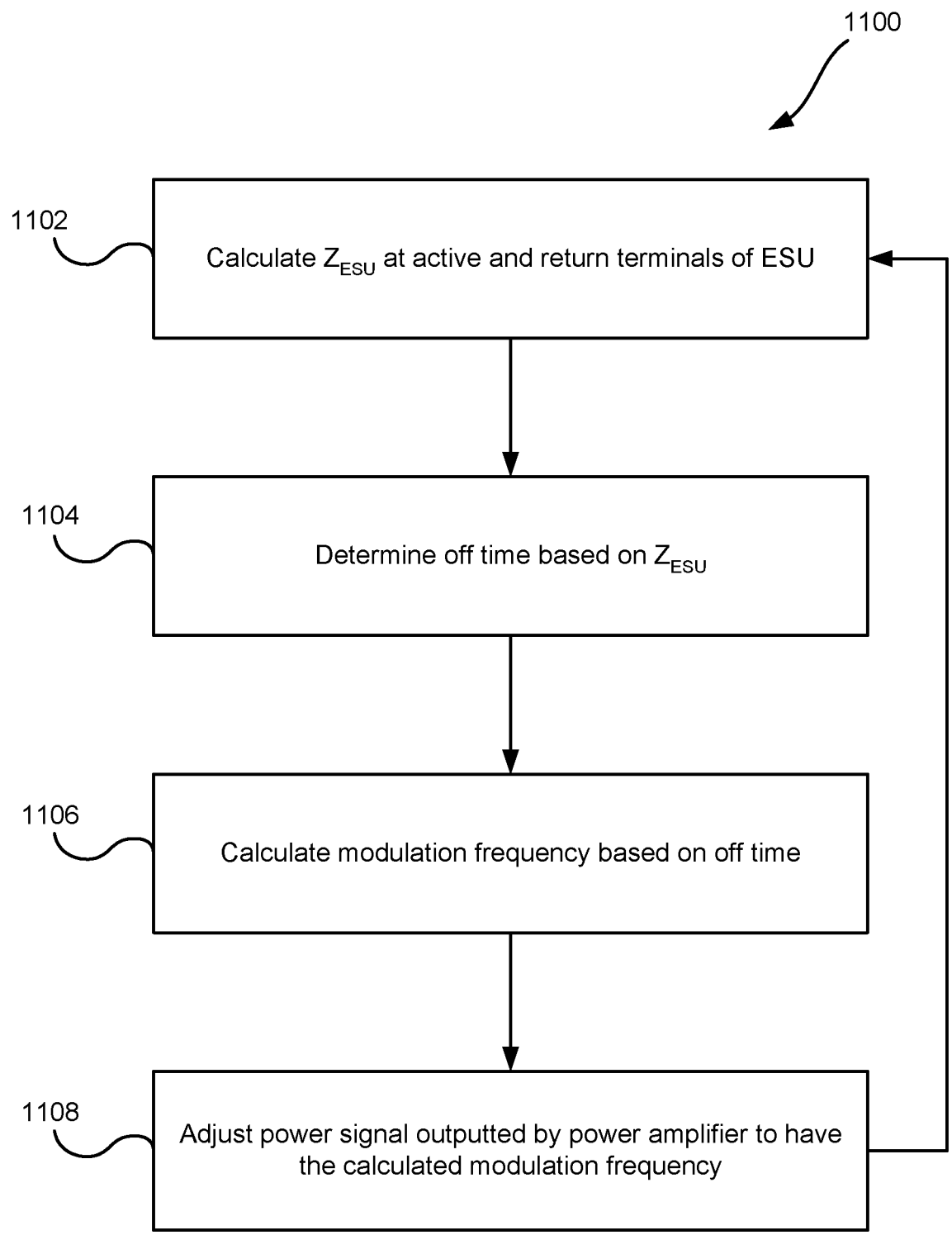
FIG. 16 is a flow chart of a dynamic RF modulation algorithm or function is shown in accordance with an embodiment of the present disclosure.

Referring to FIG. 16, the dynamic RF modulation algorithm or function is shown as method 1100 in accordance with the present disclosure. It is to be appreciated that, in one embodiment, the dynamic RF modulation algorithm or function may be executed by controller 277 periodically with a predetermined time interval of 200 ms.

In step 1102, the impedance across the active and return terminals of ESU 223 ($Z_{ESU}$) is calculated by controller 277. It is to be appreciated the $Z_{ESU}$ may be calculated as described in step 820 of method 800. In step 1104, controller 277 determines OffTime of the power signal associated with the electrosurgical energy provided to a load by applicator 310 based on the $Z_{ESU}$ calculated in step 1102. In one embodiment, controller 277 uses the $Z_{ESU}$ calculated in step 1102 to look up a corresponding OffTime in the second LUT that includes OffTimes that are based on different values for $Z_{ESU}$ to determine the OffTime based on the $Z_{ESU}$. Since, the OffTime (calculated in step 1104), $Z_{ESU}$ (calculated in step 1102) are now known by controller 277, and the Period and NumberOfPulses of the power signal (since they are fixed) are predetermined and stored in memory 278, controller 277 uses equation (10) (shown above) to calculate the ModulationFrequency, in step 1106.

After the ModulationFrequency is determined in step 1106, controller 277 adjusts the ModulationFrequency of the signal outputted by power amplifier 274 (and thus also adjusting the ModulationFrequency of the electrosurgical energy or power signal applied to the load by applicator 310) to having the determined ModulationFrequency, in step 1108. Controller 277 is configured to is configured to adjust the ModulationFrequency of the power signal outputted by power amplifier 274 by sending a control signal to oscillator 273 modulate the power signal outputted by power amplifier 274 at the calculated ModulationFrequency. After step 1108, the method 1100 is repeated. It is to be appreciated that the dynamic RF modulation algorithm or function shown in method 1100 can be performed continuously by controller 277 to dynamically adjust the ModulationFrequency of the power signal based on the calculated $Z_{ESU}$. By dynamically adjusting the ModulationFrequency of the power signal based on $Z_{ESU}$, the crest factor is also dynamically adjusted.

It is to be appreciated that by dynamically adjusting the OffTime based on the calculated $Z_{ESU}$, the dynamic RF modulation algorithm or function shown in method 1100, when executed by the controller 277, enables power generator circuit 270 of ESU 223 to provide a modulated power signal to an electrosurgical applicator 310 having a ModulationFrequency that optimizes the crest factor of the power signal or electrosurgical energy outputted by the electrosurgical applicator 310 while $Z_{ESU}$ is varying. This leads to a power signal outputted by electrosurgical applicator 310 having a low crest factor (and low $V_{PEAK}$) for low load impedances ($Z_{LOAD}$) (to support contact or cut modes of the electrosurgical applicator 310), and a high crest factor (and high $V_{PEAK}$) for high load impedances ($Z_{LOAD}$) to support plasma ignition (for contactless or plasma modes of the electrosurgical applicator 310). The OffTime values in LUT are chosen such that, when the dynamic RF modulation algorithm or function of the present disclosure is executed by controller 227, the crest factor of the power signal outputted by electrosurgical applicator 310 is automatically adjusted by controller 227, such that, a single mode of operation may be used to support both cutting modes and contactless or plasma modes under varying load impedances ($Z_{LOAD}$).

In one embodiment, both the dynamic leakage current compensation and the dynamic RF modulation algorithms or function of the present disclosure may be executed concurrently by controller 277 of ESU 223. Both algorithms or functions may be executed in parallel because their input parameters do not depend on the algorithms or functions themselves. For both algorithms or functions, the input parameter is $Z_{ESU}$ (calculated in steps 820 and 1102 of methods 800 and 1100). Adjusting the power level of the power signal delivered to the patient using the dynamic leakage current compensation algorithm or function and adjusting the MoldulationFrequency (and thus the crest factor) using the dynamic RF modulation algorithm or function will not affect $Z_{ESU}$. Both algorithms or functions being executed in parallel by controller 277 leads to adjusted and proper output power delivered to a load or patient and a dynamic crest factor based on the impedance across the active and return terminals of ESU 223 ($Z_{ESU}$). Furthermore, both algorithms or functions being executed in parallel by controller 277 enables ESU 223 and applicator 310 to work with the minimum amount of power necessary to achieve the electrosurgical effect desired. By using the minimum amount of power necessary, tissue damage is greatly reduced.

The ability to compensate for the leakage current ($i_{LEAKAGE}$, calculated in step 828 of method 800) to maintain high output RMS voltages makes it possible to implement a closed loop mode of operation that simulates, as close as possible, the original J-Plasma mode (where the transformer 220 is included in the electrosurgical applicator 310). With the dynamic leakage current compensation algorithm or function of the present disclosure, very flat power curves can be achieved up to 20 kΩ. This ensures high RMS voltages at low power settings, which eases the plasma ignition of electrosurgical applicator 310 and maintains the plasma beam generated by electrosurgical applicator 310. On the other hand, the output power in the electrosurgical range (50Ω to 2000Ω) is very accurate, which will maintain the electrosurgical effect on the tissue of the patient to a very precise degree. The closed loop control from inside the ESU 223 also gives the opportunity to quickly explore different RF configurations: such as different frequency modulations, max output RMS currents, voltages and evaluate new plasma characteristics and performances.

The dynamic leakage current compensation algorithm or function may be used also for low power cut mode applications (e.g., up to 50 Watts) with flat power curves up to 20 kΩ. This gives a user the ability to operate and do precise tissue cuts with very low power using an electrosurgical applicator 310 that is coupled to an ESU 223 that implements the dynamic leakage current compensation algorithm or function of the present disclosure. The reason for this is that the ESU 223 maintains high RMS voltage at open circuit even at a 10 Watts setting, which eases the cut process at the beginning and will minimize the dragging of blade 218 on the patient tissue.

With the introduction of the dynamic RF modulation algorithm or function of the present disclosure to the internal J-Plasma mode of operation, the physical plasma characteristics of plasma created by an electrosurgical applicator 310 coupled to an ESU 223 that implements the dynamic RF modulation algorithm or function of the present disclosure are significantly improved. The dynamic RF modulation algorithm or function dynamically changes the crest factor of the RF signal provided by the ESU 223 to the electrosurgical applicator 310 (and thus of the power signal provided to the load) based on $Z_{ESU}$. With the increase of the output impedance $Z_{ESU}$, the dynamic RF modulation algorithm or function increases the crest factor and vice versa. This performance enhances the visibility of the ionization before the plasma has been ignited. In other words, this improves the aiming capabilities of the electrosurgical applicator 310 of the plasma. As the crest factor or the peak voltages are kept higher at no load condition, the dynamic RF modulation algorithm or function increases the distance from which the plasma beam can be ignited while preserving the same output power and RMS voltages.

Another aspect of the dynamic RF modulation algorithm or function of the present disclosure is that when working with lower output impedances $Z_{ESU}$ (e.g., the electrosurgical range 100Ω to 3000Ω), the ESU 223 using the dynamic RF modulation algorithm or function decreases the crest factor of the RF and significantly improves the cutting effect on the tissue.

The combination of the closed loop together with both the dynamic leakage current compensation and dynamic RF modulation algorithms or function in one system including ESU 223 and electrosurgical applicator 310 gives the internal J-Plasma mode unique performance characteristics, i.e., the unique ability to create a hybrid mode which can cut, coagulate, and sustain a plasma beam with relatively simple and cost-effective transformerless accessory, such as, electrosurgical applicator 310 with transformer 220 removed.

Exemplary Results

Figure 17:
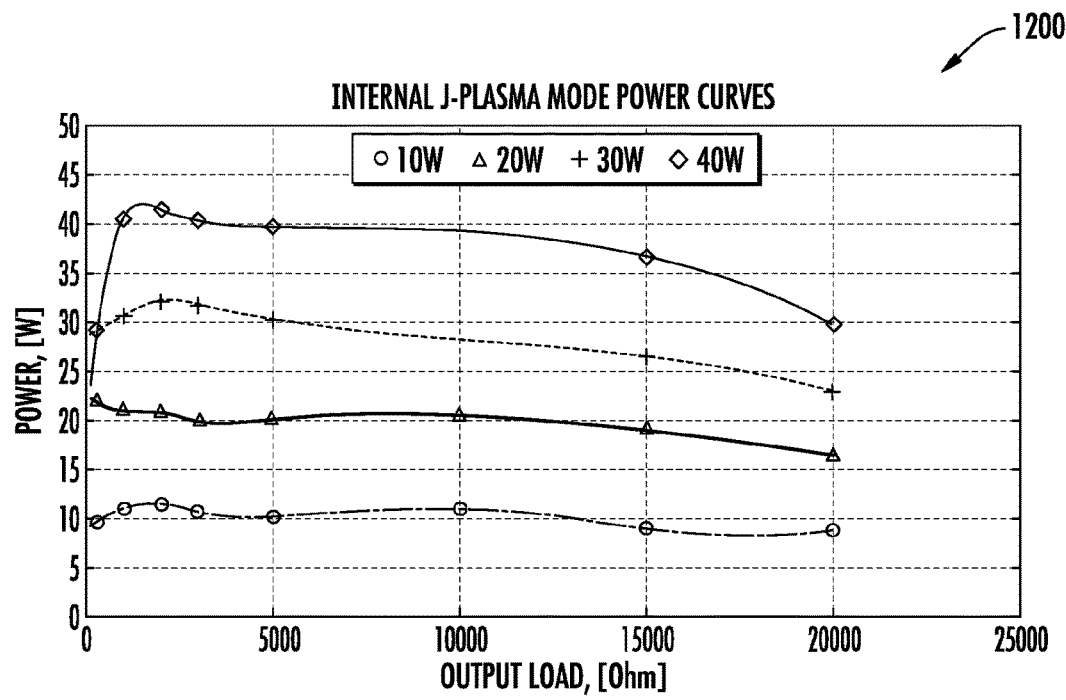
FIG. 17 is a graph of measured power curves of an electrosurgical apparatus in a ground referenced internal J-Plasma mode of operation in accordance with an embodiment of the present disclosure.
Figure 18:
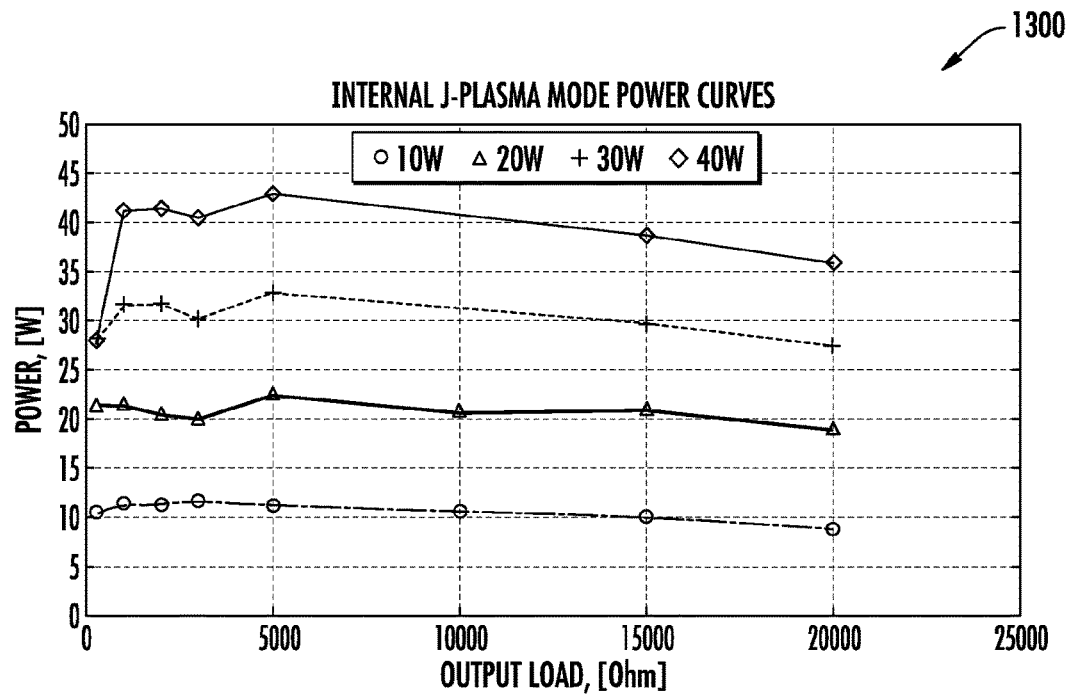
FIG. 18 is a graph of measured power curves of an electrosurgical apparatus in an isolated internal J-Plasma Mode of operation in accordance with an embodiment of the present disclosure.

Referring to FIGS. 17 and 18, graphs 1200 and 1300 are shown in accordance with the present disclosure.

Graph 1200 shows the measured power curves of the output load of electrosurgical applicator 310 coupled to ESU 223 with applicator 310 in ground referenced internal J-Plasma mode of operation with the both algorithms or functions of the present disclosure enabled in controller 277. The power curves of graph 1200 show relatively flat power curves up to 20 kΩ. When working in ground reference mode, the leakage currents depend on the position of the electrosurgical applicator 310 in space as well as the operator handling (e.g., activating the RF from hand piece or footswitch would give a slight difference in the leakage currents). However, as shown in graph 1200, with the applied algorithms or function (i.e., dynamic leakage current compensation and dynamic RF modulation algorithms functions) the power curves are still flat even at 40 W.

Graph 1300 shows the measured power curves when electrosurgical applicator 310 is in isolated internal J-Plasma Mode of operation with the both algorithms or functions of the present disclosure enabled in controller 277. As the leakage currents in isolated modes are lower, the leakage impedance LUT used in the dynamic leakage current compensation algorithm or function is also different. The mode is tweaked with an impedance LUT for an isolated accessory. The measured power curves shown in graph 1300 show that the dynamic leakage current compensation algorithm or function can be applied to any isolated mode of operation that requires low power flat curves up to 20 kΩ. The power curves are even more accurate compared to the ground referenced mode of operation shown in FIG. 17.

It is to be appreciated that the measured power curves shown in graphs 1200 and 1300 were acquired using ESU 223 and electrosurgical applicator 310 in internal J-Plasma mode of operation using the dynamic leakage current compensation and dynamic RF modulation algorithms or functions of the present disclosure. The measurements were taken using a metal plate connected through a 300 Ohm resistor to neutral electrode 292 to simulate typical tissue impedance. The streamer was measured when the metal plate was positioned 50 mm away. It is to be appreciated that a streamer is a faint discharge beam seen when the applicator is pointed away from any object, which can be used to improve pointing precision. Below, a table includes relevant plasma beam characteristics for the plasma beam measurements of graph 1200.

TABLE 2

Plasma beam measurements in ground referenced internal J-Plasma mode of operation.

PLASMA BEAM

| Power, [WQ] | Gas Flow, [slpm] | Streamer, [mm] | Ignition, [mm] |
|---|---|---|---|
| 40 | 4 | 27 | 13-14 |
| 30 | 4 | 26 | 13 |
| 20 | 3 | 21 | 11 |
| 10 | 3 | 13 | 8 |
| 7 | 3 | 5-6 | 7 |

It is to be appreciated that the various features shown and described are interchangeable, that is, a feature shown in one embodiment may be incorporated into another embodiment. While the disclosure has been shown and described with reference to certain preferred embodiments thereof, it will be understood by those skilled in the art that various changes in form and detail may be made therein without departing from the spirit and scope of the disclosure as defined by the appended claims. Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims. It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An electrosurgical generator comprising:
a power generator circuit configured to output electrosurgical energy, the power generator circuit including a power supply configured to supply power to a power amplifier that generates the electrosurgical energy and an oscillator configured to modulate the electrosurgical energy generated by power amplifier at different frequencies;
an active terminal configured to be coupled to an electrosurgical applicator via a cable, the active terminal configured to provide the electrosurgical energy to the electrosurgical applicator, the electrosurgical applicator providing the electrosurgical energy to a load;
a return terminal configured to provide a return path for the electrosurgical energy applied to the load;

a sensor coupled to the active terminal and return terminal, the sensor configured to sample the electrosurgical energy at the active terminal and return terminal for voltage data and current data; and a controller configured to control the power generator circuit, wherein the controller:

determines a leakage impedance from the sampled voltage data and current data across the active terminal and return terminal, determines a leakage current associated with the electrosurgical applicator and the cable, the leakage current determined from the determined leakage impedance, determines a power level of the electrosurgical energy delivered to the load by the electrosurgical applicator, the power level determined from the determined leakage current, and responsive to determining that the power level of the delivered electrosurgical energy does not match a predetermined power level, adjusts the power level of electrosurgical energy outputted by the power generator circuit to match the predetermined power level by providing a first control signal to the power supply to increase or decrease the power supplied to the power amplifier.

2. The electrosurgical generator of claim 1, wherein the controller is configured to determine a Root Mean Square (RMS) voltage across the active terminal and return terminal based on the sampled voltage data and to determine an output RMS current of the electrosurgical energy at the active terminal based on the sampled current data.

3. The electrosurgical generator of claim 2, wherein the controller is configured to determine the RMS voltage by calculating a moving-average RMS for the sampled voltage data and scaling the moving-average RMS for the sampled voltage by a voltage scaling coefficient and the controller is configured to determine the RMS current by calculating a moving-average RMS for the sampled current data and scaling the moving-average RMS for the sampled current data by a current coefficient.

4. The electrosurgical generator of claim 2, wherein the controller is configured to determine an impedance across the active terminal and return terminal based on the RMS voltage and the RMS current.

5. The electrosurgical generator of claim 4, wherein the controller is configured to determine the leakage current by dividing the RMS voltage by the leakage impedance, the leakage impedance being an equivalent parallel impedance of the electrosurgical applicator and the cable.

6. The electrosurgical generator of claim 5, further comprising a memory including a look-up table, the look-up table including leakage impedance values corresponding to values of impedance across the active and return terminals, wherein the controller is configured to determine the leakage impedance by retrieving a leakage impedance value corresponding to the determined impedance across the active and return terminals.

7. The electrosurgical generator of claim 6, wherein the leakage impedance values in the look-up table are calculated according to the following formula:

$$Z_{ESU} = \frac{Z_{LEAKAGE} \times Z_{LOAD}}{Z_{LEAKAGE} + Z_{LOAD}}$$

where $Z_{ESU}$ is the impedance across the active and return terminals, $Z_{LEAKAGE}$ is the leakage impedance, and $Z_{LOAD}$ is an impedance of the load.

8. The electrosurgical generator of claim 4, wherein the controller is further configured to:

calculate a modulation frequency of the electrosurgical energy to be delivered to the load by the electrosurgical applicator based on the impedance across the active terminal and return terminal, the calculated modulation frequency being continuously updated to dynamically control a crest factor of the electrosurgical energy while the impedance across the active terminal and return terminal is varying, and adjust the electrosurgical energy outputted by the power generator circuit to have the calculated modulation frequency by providing a second control signal to the oscillator to modulate the electrosurgical energy outputted by the power amplifier.

9. The electrosurgical generator of claim 1, wherein the controller is configured to determine a voltage across a length of the cable based on an equivalent series impedance of the cable.

10. The electrosurgical generator of claim 9, wherein the power level of the electrosurgical energy delivered to the load is further determined based on the voltage across the length of the cable.

11. The electrosurgical generator of claim 1, wherein the controller is configured to perform the determining and the adjusting periodically to dynamically adjust the power level of the electrosurgical energy delivered to the load to compensate for the determined leakage current.

12. An electrosurgical generator comprising:

a power generator circuit configured to output electrosurgical energy, the power generator circuit including a power supply configured to supply power to a power amplifier that generates the electrosurgical energy and an oscillator configured to modulate the electrosurgical energy generated by power amplifier at different frequencies;

an active terminal configured to be coupled to an electrosurgical applicator via a cable, the active terminal configured to provide the electrosurgical energy to the electrosurgical applicator, the electrosurgical applicator providing the electrosurgical energy to a load;

a return terminal configured to provide a return path for the electrosurgical energy applied to the load;

a sensor coupled to the active terminal and return terminal, the sensor configured to sample the electrosurgical energy at the active terminal and return terminal for voltage data and current data; and a controller configured to control the power generator circuit, wherein the controller:

determines an impedance across the active terminal and return terminal, the impedance based on the sampled voltage data and current data, calculates a modulation frequency of the electrosurgical energy outputted by the power generator circuit, the modulation frequency determined from the determined impedance at the active terminal and return terminal, the calculated modulation frequency being continuously updated to dynamically control a crest factor of the electrosurgical energy while the impedance across the active terminal and return terminal is varying, the calculated modulation frequency being updated with varying impedance values, and adjusts the electrosurgical energy outputted by the power generator circuit to match the calculated modulation frequency by providing a first control signal to the oscillator to modulate the electrosurgical energy outputted by the power amplifier.

13. The electrosurgical generator of claim 12, wherein the controller is configured to determine a Root Mean Square (RMS) voltage across the active terminal and return terminal based on the sampled voltage data and to determine an output RMS current of the electrosurgical energy at the active terminal based on the sampled current data.

14. The electrosurgical generator of claim 13, wherein the controller is configured to determine the RMS voltage by calculating a moving-average RMS for the sampled voltage data and scaling the moving-average RMS for the sampled voltage by a voltage scaling coefficient and the controller is configured to determine the RMS current by calculating a moving-average RMS for the sampled current data and scaling the moving-average RMS for the sampled current data by a current coefficient.

15. The electrosurgical generator of claim 14, wherein the controller is configured to determine impedance across the active and return terminals by dividing the determined RMS voltage by the determined RMS current.

16. The electrosurgical generator of claim 12, wherein the modulation frequency is determined based on an off time of the electrosurgical energy outputted by the power generator circuit.

17. The electrosurgical generator of claim 16, further comprising a memory including a look-up table, the look-up table including modulation frequency values of impedance across the active and return terminals, wherein the controller is configured to determine the off time by retrieving an off time value corresponding to the determined impedance across the active and return terminals.

18. The electrosurgical generator of claim 16, wherein the modulation frequency is determined by the controller according to the following formula:

$$ModulationFrequency = \frac{1}{Period \times NumberOfPulses + OffTime}$$

wherein, the Period and the Number Of Pulses in the formula above correspond to a modulation cycle of the electrosurgical energy and are predetermined values stored in a memory of the electrosurgical generator.

19. The electrosurgical generator of claim 12, wherein the controller is configured to perform the determining, calculating and the adjusting periodically to dynamically adjust the modulation frequency of the electrosurgical energy outputted by the power generator circuit.

20. The electrosurgical generator of claim 12, wherein the controller is further configured to:
determine a leakage current associated with the electrosurgical applicator and the cable, the leakage current based on the leakage impedance across the active terminal and return terminal, and a power level of the electrosurgical energy delivered to the load by the electrosurgical applicator based on determined leakage current, and
adjust the electrosurgical energy outputted by the power generator circuit to match the predetermined power level if it is determined that the power level of the electrosurgical energy delivered to the load does not match the predetermined power level by providing a second control signal to the power supply to increase or decrease the power supplied to the power amplifier.

* * * * *